US011179450B2

(12) United States Patent
Shiku et al.

(10) Patent No.: US 11,179,450 B2
(45) Date of Patent: Nov. 23, 2021

(54) LONG CHAIN ANTIGEN CONTAINING INTEREPITOPE SEQUENCE THAT PROMOTES ANTIGEN PRESENTATION TO T CELLS

(71) Applicants: MIE UNIVERSITY, Tsu (JP); KYOTO UNIVERSITY, Kyoto (JP)

(72) Inventors: Hiroshi Shiku, Tsu (JP); Naozumi Harada, Tsu (JP); Daisuke Muraoka, Tsu (JP); Kazunari Akiyoshi, Kyoto (JP)

(73) Assignees: MIE UNIVERSITY, Tsu (JP); KYOTO UNIVERSITY, Kyoto (JP)

( * ) Notice: Subject to any disclaimer, the term of this patent is extended or adjusted under 35 U.S.C. 154(b) by 174 days.

(21) Appl. No.: 16/035,922

(22) Filed: Jul. 16, 2018

(65) Prior Publication Data

US 2019/0015490 A1 Jan. 17, 2019

Related U.S. Application Data

(63) Continuation of application No. 15/026,841, filed as application No. PCT/JP2014/076286 on Oct. 1, 2014, now abandoned.

(30) Foreign Application Priority Data

Oct. 1, 2013 (JP) ................................ 2013-206639

(51) Int. Cl.

*A61K 39/00* (2006.01)
*A61K 39/015* (2006.01)
*A61K 39/12* (2006.01)
*A61K 47/36* (2006.01)
*A61K 9/00* (2006.01)

(52) U.S. Cl.

CPC ........ *A61K 39/0011* (2013.01); *A61K 39/015* (2013.01); *A61K 39/12* (2013.01); *A61K 9/0019* (2013.01); *A61K 47/36* (2013.01); *A61K 2039/55583* (2013.01); *A61K 2039/6087* (2013.01); *C12N 2710/16122* (2013.01); *C12N 2710/16134* (2013.01)

(58) Field of Classification Search

CPC ........................... A61K 38/00; A61K 39/0011
See application file for complete search history.

(56) References Cited

U.S. PATENT DOCUMENTS 6,656,481 B1 12/2003 Shiku et al.
7,745,391 B2 * 6/2010 Mintz .................... A61P 31/00 514/19.3
8,158,131 B2 4/2012 Apt et al.
9,422,356 B2 8/2016 Lee et al.
2004/0198684 A1 10/2004 Shiku
2006/0183669 A1 8/2006 Hansen et al.
2008/0166369 A1 7/2008 Shiku et al.
2008/0187535 A1 8/2008 Blais et al.
2009/0246213 A1 10/2009 Shiku
2010/0029912 A1 2/2010 Blais et al.
2010/0062011 A1 3/2010 Yano
2012/0029175 A1 2/2012 Nagura et al.
2014/0322344 A1 10/2014 Shiku et al.
2015/0011729 A1 * 1/2015 Ranum .................. C12N 9/12 530/326
2016/0367651 A1 * 12/2016 Shiku ...................... A61P 35/00
2017/0233747 A1 * 8/2017 Govindappa ........... C07K 7/08 435/69.7
2017/0266079 A1 9/2017 Hanotin et al.
2017/0267783 A1 9/2017 Nezu et al.

FOREIGN PATENT DOCUMENTS

| | | | | |
|---|---|---|---|---|
| EP | 1428879 | A | 6/2004 | |
| EP | 1579870 | A | 9/2005 | |
| EP | 1834650 | A1 | 9/2007 | |
| EP | 2006302 | A2 | 12/2008 | |
| JP | S6169801 | A | 4/1986 | |
| JP | H03292301 | A | 12/1991 | |
| JP | H0797333 | A | 4/1995 | |
| JP | 2002255995 | A | 9/2002 | |
| JP | 4033497 | B2 | 1/2008 | |
| WO | 2001057182 | A2 | 8/2001 | |
| WO | WO-0157182 | A2 * | 8/2001 | ........... C12N 9/6424 |
| WO | WO-0164835 | A2 * | 9/2001 | ............. C07K 14/47 |
| WO | 2007097251 | A1 | 8/2007 | |
| WO | 2007119859 | A1 | 10/2007 | |
| WO | 2008089074 | A | 7/2008 | |
| WO | WO-2010115033 | A2 * | 10/2010 | ............... C12N 9/12 |
| WO | 2011090065 | A1 | 7/2011 | |

(Continued)

OTHER PUBLICATIONS

Database UNIPROT accession No. A7Y7E6_STYHA (Oct. 23, 2007) (pp. 1-3).*
Database UNIPROT accession No. Q9K2E1_CHLPN (Oct. 1, 2000) (pp. 1-3).*
Defoort et al. (Int. J. Pept. Protein Res. Sep.-Oct. 1992; 40 (3-4): 214-21).*
Akiyoshi, K., et al., J. Proc. Japan. Acad., 1995; 71 (71B): p. 15.
Akiyoshi, K., et al., Macromolecules., 1993; 26(12): pp. 3062-3068.
Behrens, G. et al., Immunol. Cell Biol. 2004; 82(1): pp. 84-90.
Bergmann C. et al."Flanking residues Alter Antigenicity and Immunogenicity of Multi-Unit CTL Epitopes", The Journal of Immunology, The American Association of Immunologists, vol. 157, No. 8, Jan. 1, 1996 (Jan. 1, 1996), pp. 3242-3249, XP002904287, ISSN: 0022-1767.

(Continued)

*Primary Examiner* — Stephen L Rawlings
(74) *Attorney, Agent, or Firm* — J-Tek Law PLLC; Jeffrey D. Tekanic; Scott T. Wakeman

(57) ABSTRACT

A long-chain peptide antigen includes a plurality of epitopes. An interepitope sequence located between two of the plurality of epitopes contains four to ten consecutive tyrosines. The long-chain peptide antigen may be administered to a patient together with a hydrophobized polysaccharide, such as cholesterol-modified pullulan, and/or an adjuvant, such as CpG oligo DNA.

23 Claims, 11 Drawing Sheets

Specification includes a Sequence Listing.

(56) References Cited

FOREIGN PATENT DOCUMENTS

| WO | 2013031882 A1 | 3/2013 | |
|---|---|---|---|
| WO | WO-2015050158 A1 * | 4/2015 | ........... A61K 39/015 |

OTHER PUBLICATIONS

Bodey et al., Anticancer Research. 2000; 20: 2665-2676.
Brewer, J. M., et al., J. Immunol. 1998; 161: pp. 4000-4007.
Byrd-Leifer, C. A., et al., Eur. J. Immunol. 2001; 31(8): pp. 2448-2457.
Choudhury et al., J. Reprod. Immunol. 2009; 79: 137-47.
Daisuke Muraoka, et al. "Nanogel-Based Immunologically Stealth Vaccine Targets Macrophages in the Medulla of Lymph Node and Induces Potent Antitumor Immunity", ACS NANO,vol. 8, No. 9, Sep. 2, 2014 (Sep. 2, 2014), pp. 9209-9218, XP55357955 us ISSN: 1936-0851.
Depla et al., J. Virol. 2008; 82: 435-50.
Dhodapkar, M., et al., Induction of Antigen-Specific Immunity with a Vaccine Targeting NY-ESO-1 to the Dendritic Cell Receptor DEC-205, Science Translational Medicine 6 (232), 232ra51 1-9, published Apr. 16, 2014.
Elliott et al., Development. Apr. 2006; 133 (7): 1311-22.
Finn, O., The dawn of vaccines for cancer prevention, Nature Reviews / Immunology, doi:10.1038/nri.2017.140, published online Dec. 27, 2017.
Gallou et al., Oncotarget. Sep. 13, 2016; 7 (37): 59417-28.
Goldberg, A. L., et al., Mol. Immunol. 2002; 39(3-4): 147-64.
Wang et al., Scand. J. Immunol. Sep. 2004; 60 (3): 219-25.
Gu, X. G., et al., Cancer Res., 1998; 58(15): pp. 3385-3390.
Hasegawa, K., et al., Clin. Cancer Res., 2006; 12(6): pp. 1921-1927.
Henriksen-Lacey, M., et al., J. Controlled Release. 2011; 154(2): pp. 131-137.
Holland, C. J., et al., Front Immunol. 2013; 4:172.
Ikuta et al., Blood. 2002; 99: 3717-24.
Kakimi, Kazuhiro et al: "A phase I study of vaccination with NY-ESO-1f peptide mixed with Picibanil OK-432 and MontanideISA-51 in patients with cancers expressing the NY-ESO-1 antigen", International Journal of Cancer,vol. 129, No. 12, Dec. 2011 (Dec. 2011), pp. 2836-2846.
Kitano et al.; Clin Cancer Res 12:7397-05, 2006.
Kollessery,G., et al., "Tumor-specific peptide based vaccines containing the conformationally biased, response-selective C5a agonists EP54 and EP67 protect against large B cell lymphoma in a syngeneic murine model", Vaccine, Aug. 11, 2011, vol. 29, No. 35, p. 5904-5910 Abstract, p. 5905, paragraph of '2.1. Vaccine design and Synthesis'.
Kong, L. Y., et al., Clin. Cancer Res. 2008; 14(18): pp. 5759-5768.
Kwon et al., Biochim. Biophys. Acta. 1998; 1388: 239-46.
Livingston et al., J. Immunol. 2002; 168: 5499-506.
Lollini et al., Curr. Cancer Drug Targets. May 2005; 5 (3): 221-228.
Lollini et al., Trends Immunol. Feb. 2003; 24 (2): 62-66.
Masuko,K., et al., "Artificially synthesized helper/killer-hybrid epitope long peptide (H/K-Help): Preparation and Immunological analysis of vaccine efficacy", Immunol. Lett., vol. 163, No. I, p. 102-112, [online], Dec. 3, 2014, [Dec. 15, 2014 retrieval date].
Melief Cornelis J M et al: "Effective therapeutic anticancer vaccines based on precision guiding of cytolytic T lymphocytes.", Immunological Reviews Oct. 2002, vol. 188, Oct. 2002 (Oct. 2002), pp. 177-182, ISSN: 0105-2896.
Melief, C. J. M., & van der Burg, S. H., Nature Rev. Cancer, 2008; 8(5): pp. 351-360.
Mildenberger et al., Curr. Opin. Neurol. Oct. 4, 2017; electronically published ahead of print; pp. 1-9.
Morishita et al., Structure. Oct. 12, 2011; 19 (10): 1496-508.
Muraoka, D., et al., J. Immunol. 2010; 185(6): pp. 3768-3776.
Muraoka, D., et al., Vaccine. 2013; 31: 2110-2118.
Nakanishi, T., et al., J. Controlled Release. 1999; 61: pp. 233-240.
Nezafat,N., et al., "A novel multi-epitope peptide vaccine against cancer: An in silico approach", J. Theor. Biol., May 21, 2014, vol. 349, p. 121-134 Abstract.
Nishikawa, T., et al., Macromolecules. 1994; 27(26): pp. 7654-7659.
Ohtake,J., et al., "Identification of novel helper epitope peptides of Survivin cancerassociated antigen appicable to developinghelper/killer-hybrid epitope long peptide cancer vaccine", Immunol. Lett., Sep. 2014., vol. 161, No. I, p. 20-30 Abstract.
Partial European Search Report from the European Patent Office dated May 2, 2017 in related EP application No. 14 85 0811 .2, including European Search Opinion, Supplemental Partial European Search Report, and examined claims 1-9.
Prehn, Cancer Cell Int. Aug. 1, 2005; 5 (1 ): 25; pp. 1-5.
Ribas, A. et al. J. Clin. Oncol. 2003; 21(12): pp. 2415-2432.
Sette et al., Tissue Antigens. 2002: 59:443-51.
Shariat et al., Iran J. Basic Med. Sci. May 2015; 18 (5): 506-13.
Shen L. & Rock K. L., Curr. Opin. Immunol. 2006; 18(1): pp. 85-91.
Shiku H., "Multicenter clinical study of multivalent cancer vaccine with new antigen protein delivery system", Ministry of Education, Culture, Sports, Science and Technology, Gan TR Jigyo 3 Kai Gan Seika Hokokukai Shorokushu, published at http://www.ctrp.mext.go.jp/pdf/3rd/3rd_abreport_04_shiku.pdf, Mar. 3, 2007, including English abstract attached thereto.
Shiku, H. Int. J. Hematol. 2003; 77(5): pp. 435-438.
Slinghuff et al., Cancer Immunol. Immunother. Mar. 2000; 48 (12): 661-672.
Takahashi,N., et al., "First clinical trial of cancer vaccine therapy with artificially synthesized helper/killer-hybrid epitope long peptide of MAGE-A4 cancer antigen", Cancer Sci., Jan. 2012, vol. 103, No. I, p. 150-153.
Tsuji, T., et al., Antibody-Targeted NY-ESO-1 to Mannose Receptor or DEC-205 in Vitro Elicits Dual Human CD8+ and CD4+ T Cell Responses with Broad Antigen Specificity, J Immunol 2011; 186:1218-1227; Prepublished online Dec. 13, 2010.
English Translation of Written Opinion of the International Searching Authority in PCT/JP2014/076286.
Uenaka, A. et al., "T cell immunomonitoring and tumor responses in patients immunized with a complex of cholesterol-bearing hydrophobized pullulan (CHP) and NY-ESO-1 protein", Cancer Immunity, vol. 7, p. 9, electronically published Apr. 19, 2007.
Van der Burg, S, et al., Vaccines for established cancer: overcoming the challenges posed by immune evasion, Nature Reviews / Cancer (2016) 16: 219-233, published online Mar. 11, 2016.
English translation of International Search Report for parent application No. PCT/JP2014/076286.
Beißbarth T, et al., "A systematic approach for comprehensive T-cell epitope discovery using peptide libraries", Bioinformatics, vol. 21 Suppl. 1 2005, pp. i29-i37, doi:10.1093/bioinformatics/bti1013.
Patronov A, et al., "T-cell epitope vaccine design by immunoinformatics", Open Biol 3: 120139, 2013, http://dx.doi.org/10.1098/rsob.120139.
Sanchez-Trincado JL, et al., "Fundamentals and Methods for T- and B-Cell Epitope Prediction", Journal of Immunology Research, vol. 2017, Article ID 2680160, 14 pages, https://doi.org/10.1155/2017/2680160.
Sharma G. et al., "T-cell epitope discovery technologies", Human Immunology 75 (2014) pp. 514-519.
Tian Y. et al., "A Review on T Cell Epitopes Identified Using Prediction and Cell-Mediated Immune Models for Mycobacterium tuberculosis and Bordetella pertussis", Front. Immunol. 9:2778 (2018), doi: 10.3389/fimmu.2018.02778.

* cited by examiner

SEQUENCE LISTING

<160> NUMBER OF SEQ ID NOS: 35

<210> SEQ ID NO 1

-continued

```
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 1

Ser Asn Pro Ala Arg Tyr Glu Phe Leu Tyr Tyr Tyr Tyr Tyr Gln
1               5                   10                  15

Tyr Ile His Ser Ala Asn Val Leu Tyr Tyr Tyr Tyr Tyr Arg Gly
            20                  25                  30

Pro Glu Ser Arg Leu Leu
        35

<210> SEQ ID NO 2
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 2

Ser Asn Pro Ala Arg Tyr Glu Phe Leu Gly Gly Gly Gly Gly Gln
1               5                   10                  15

Tyr Ile His Ser Ala Asn Val Leu Gly Gly Gly Gly Gly Arg Gly
            20                  25                  30

Pro Glu Ser Arg Leu Leu
        35

<210> SEQ ID NO 3
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 3

Ser Asn Pro Ala Arg Tyr Glu Phe Leu Pro Pro Pro Pro Pro Gln
1               5                   10                  15

Tyr Ile His Ser Ala Asn Val Leu Pro Pro Pro Pro Pro Arg Gly
            20                  25                  30

Pro Glu Ser Arg Leu Leu
        35

<210> SEQ ID NO 4
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 4

Ser Asn Pro Ala Arg Tyr Glu Phe Leu Thr Thr Thr Thr Thr Gln
1               5                   10                  15

Tyr Ile His Ser Ala Asn Val Leu Thr Thr Thr Thr Thr Arg Gly
            20                  25                  30
```

Pro Glu Ser Arg Leu Leu
        35

<210> SEQ ID NO 5
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 5

Arg Gly Pro Glu Ser Arg Leu Leu Tyr Tyr Tyr Tyr Tyr Tyr Ser Asn
1               5                   10                  15

Pro Ala Arg Tyr Glu Phe Leu Tyr Tyr Tyr Tyr Tyr Tyr Gln Tyr Ile
            20                  25                  30

His Ser Ala Asn Val Leu
        35

<210> SEQ ID NO 6
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 6

Arg Gly Pro Glu Ser Arg Leu Leu Gly Gly Gly Gly Gly Gly Ser Asn
1               5                   10                  15

Pro Ala Arg Tyr Glu Phe Leu Gly Gly Gly Gly Gly Gly Gln Tyr Ile
            20                  25                  30

His Ser Ala Asn Val Leu
        35

<210> SEQ ID NO 7
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 7

Arg Gly Pro Glu Ser Arg Leu Leu Pro Pro Pro Pro Pro Pro Ser Asn
1               5                   10                  15

Pro Ala Arg Tyr Glu Phe Leu Pro Pro Pro Pro Pro Pro Gln Tyr Ile
            20                  25                  30

His Ser Ala Asn Val Leu
        35

<210> SEQ ID NO 8
<211> LENGTH: 38
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 8

Gln Tyr Ile His Ser Ala Asn Val Leu Tyr Tyr Tyr Tyr Tyr Tyr Arg

-continued

```
                1               5                  10                  15

Gly Pro Glu Ser Arg Leu Leu Tyr Tyr Tyr Tyr Tyr Ser Asn Pro
                20                  25                  30

Ala Arg Tyr Glu Phe Leu
        35

<210> SEQ ID NO 9
<211> LENGTH: 28
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 9

Ser Asn Pro Ala Arg Tyr Glu Phe Leu Tyr Gln Tyr Ile His Ser Ala
1               5                   10                  15

Asn Val Leu Tyr Arg Gly Pro Glu Ser Arg Leu Leu
                20                  25

<210> SEQ ID NO 10
<211> LENGTH: 30
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 10

Ser Asn Pro Ala Arg Tyr Glu Phe Leu Tyr Tyr Gln Tyr Ile His Ser
1               5                   10                  15

Ala Asn Val Leu Tyr Tyr Arg Gly Pro Glu Ser Arg Leu Leu
                20                  25                  30

<210> SEQ ID NO 11
<211> LENGTH: 32
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 11

Ser Asn Pro Ala Arg Tyr Glu Phe Leu Tyr Tyr Tyr Gln Tyr Ile His
1               5                   10                  15

Ser Ala Asn Val Leu Tyr Tyr Tyr Arg Gly Pro Glu Ser Arg Leu Leu
                20                  25                  30

<210> SEQ ID NO 12
<211> LENGTH: 34
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 12

Ser Asn Pro Ala Arg Tyr Glu Phe Leu Tyr Tyr Tyr Tyr Gln Tyr Ile
1               5                   10                  15

His Ser Ala Asn Val Leu Tyr Tyr Tyr Tyr Arg Gly Pro Glu Ser Arg
                20                  25                  30
```

Leu Leu

<210> SEQ ID NO 13
<211> LENGTH: 36
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 13

Ser Asn Pro Ala Arg Tyr Glu Phe Leu Tyr Tyr Tyr Tyr Gln Tyr
1               5                   10                  15

Ile His Ser Ala Asn Val Leu Tyr Tyr Tyr Tyr Arg Gly Pro Glu
            20                  25                  30

Ser Arg Leu Leu
        35

<210> SEQ ID NO 14
<211> LENGTH: 42
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 14

Ser Asn Pro Ala Arg Tyr Glu Phe Leu Tyr Tyr Tyr Tyr Tyr Tyr
1               5                   10                  15

Tyr Gln Tyr Ile His Ser Ala Asn Val Leu Tyr Tyr Tyr Tyr Tyr
            20                  25                  30

Tyr Tyr Arg Gly Pro Glu Ser Arg Leu Leu
        35                  40

<210> SEQ ID NO 15
<211> LENGTH: 46
<212> TYPE: PRT
<213> ORGANISM: Artificial
<220> FEATURE:
<223> OTHER INFORMATION: Long chain peptide antigen, containing three
      types of mouse CD8+ T cell epitope sequences (MA p265, NY p81, and
      mERK2 9m)

<400> SEQUENCE: 15

Ser Asn Pro Ala Arg Tyr Glu Phe Leu Tyr Tyr Tyr Tyr Tyr Tyr
1               5                   10                  15

Tyr Tyr Tyr Gln Tyr Ile His Ser Ala Asn Val Leu Tyr Tyr Tyr
            20                  25                  30

Tyr Tyr Tyr Tyr Tyr Tyr Arg Gly Pro Glu Ser Arg Leu Leu
        35                  40                  45

<210> SEQ ID NO 16
<211> LENGTH: 40
<212> TYPE: PRT
<213> ORGANISM: Homo sapience

<400> SEQUENCE: 16

Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser Leu Ala
            20                  25                  30

Gln Asp Ala Pro Pro Leu Pro Val
        35              40

<210> SEQ ID NO 17
<211> LENGTH: 33
<212> TYPE: PRT
<213> ORGANISM: Artificial
<220> FEATURE:
<223> OTHER INFORMATION: Long chain peptide antigen, containing a mouse
      CD8+ T cell epitope sequence (NY p81) and a mouse CD4+ T cell
      epitope sequence (NY p91)

<400> SEQUENCE: 17

Gly Pro Glu Ser Arg Leu Leu Tyr Tyr Tyr Tyr Tyr Tyr Leu Ala
1               5                   10                  15

Met Pro Phe Ala Thr Pro Met Glu Ala Glu Leu Ala Arg Arg Ser Leu
            20                  25                  30

Ala

<210> SEQ ID NO 18
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 18

Ser Leu Leu Met Trp Ile Thr Gln Cys Ala Ala Ala Ala Ala Asn
1               5                   10                  15

Tyr Lys Arg Cys Phe Pro Val Ile Ala Ala Ala Ala Ala Cys Met
            20                  25                  30

Thr Trp Asn Gln Met Asn Leu
        35

<210> SEQ ID NO 19
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 19

Ser Leu Leu Met Trp Ile Thr Gln Cys Glu Glu Glu Glu Glu Asn
1               5                   10                  15

Tyr Lys Arg Cys Phe Pro Val Ile Glu Glu Glu Glu Glu Cys Met
            20                  25                  30

Thr Trp Asn Gln Met Asn Leu
        35

<210> SEQ ID NO 20
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 20

Ser Leu Leu Met Trp Ile Thr Gln Cys Gly Gly Gly Gly Gly Asn

```
1               5                   10                  15

Tyr Lys Arg Cys Phe Pro Val Ile Gly Gly Gly Gly Gly Cys Met
            20                  25                  30

Thr Trp Asn Gln Met Asn Leu
            35

<210> SEQ ID NO 21
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 21

Ser Leu Leu Met Trp Ile Thr Gln Cys His His His His His Asn
1               5                   10                  15

Tyr Lys Arg Cys Phe Pro Val Ile His His His His His Cys Met
            20                  25                  30

Thr Trp Asn Gln Met Asn Leu
            35

<210> SEQ ID NO 22
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 22

Ser Leu Leu Met Trp Ile Thr Gln Cys Asn Asn Asn Asn Asn Asn
1               5                   10                  15

Tyr Lys Arg Cys Phe Pro Val Ile Asn Asn Asn Asn Asn Cys Met
            20                  25                  30

Thr Trp Asn Gln Met Asn Leu
            35

<210> SEQ ID NO 23
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 23

Ser Leu Leu Met Trp Ile Thr Gln Cys Pro Pro Pro Pro Pro Asn
1               5                   10                  15

Tyr Lys Arg Cys Phe Pro Val Ile Pro Pro Pro Pro Pro Cys Met
            20                  25                  30

Thr Trp Asn Gln Met Asn Leu
            35

<210> SEQ ID NO 24
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
```

MA4 p143, and WT1 p235)

<400> SEQUENCE: 24

Ser Leu Leu Met Trp Ile Thr Gln Cys Gln Gln Gln Gln Gln Asn
1               5                   10                  15

Tyr Lys Arg Cys Phe Pro Val Ile Gln Gln Gln Gln Gln Cys Met
            20                  25                  30

Thr Trp Asn Gln Met Asn Leu
        35

<210> SEQ ID NO 25
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 25

Ser Leu Leu Met Trp Ile Thr Gln Cys Ser Ser Ser Ser Ser Asn
1               5                   10                  15

Tyr Lys Arg Cys Phe Pro Val Ile Ser Ser Ser Ser Ser Cys Met
            20                  25                  30

Thr Trp Asn Gln Met Asn Leu
        35

<210> SEQ ID NO 26
<211> LENGTH: 39
<212> TYPE: PRT
<213> ORGANISM: Artificial
<220> FEATURE:
<223> OTHER INFORMATION: Long chain peptide antigen, containing three
      types of human CD8+ T cell recognition epitope sequences (NY p157,
      MA4 p143, and WT1 p235)

<400> SEQUENCE: 26

Ser Leu Leu Met Trp Ile Thr Gln Cys Tyr Tyr Tyr Tyr Tyr Asn
1               5                   10                  15

Tyr Lys Arg Cys Phe Pro Val Ile Tyr Tyr Tyr Tyr Tyr Cys Met
            20                  25                  30

Thr Trp Asn Gln Met Asn Leu
        35

<210> SEQ ID NO 27
<211> LENGTH: 9
<212> TYPE: PRT
<213> ORGANISM: Artificial
<220> FEATURE:
<223> OTHER INFORMATION: Peptide sequence containing mouse CD8+ T cell
      epitope, MA p265

<400> SEQUENCE: 27

Ser Asn Pro Ala Arg Tyr Glu Phe Leu
1               5

<210> SEQ ID NO 28
<211> LENGTH: 9
<212> TYPE: PRT
<213> ORGANISM: Artificial
<220> FEATURE:
<223> OTHER INFORMATION: Peptide sequence containing mouse CD8+ T cell
      epitope, mERK2 9m

<400> SEQUENCE: 28

```
Gln Tyr Ile His Ser Ala Asn Val Leu
1               5
```

<210> SEQ ID NO 29
<211> LENGTH: 8
<212> TYPE: PRT
<213> ORGANISM: Artificial
<220> FEATURE:
<223> OTHER INFORMATION: Peptide sequence containing mouse CD8+ T cell
      epitope, NY p81

<400> SEQUENCE: 29

```
Arg Gly Pro Glu Ser Arg Leu Leu
1               5
```

<210> SEQ ID NO 30
<211> LENGTH: 9
<212> TYPE: PRT
<213> ORGANISM: Artificial
<220> FEATURE:
<223> OTHER INFORMATION: Peptide sequence containing human CD8+ T cell
      epitope, NY P157

<400> SEQUENCE: 30

```
Ser Leu Leu Met Trp Ile Thr Gln Cys
1               5
```

<210> SEQ ID NO 31
<211> LENGTH: 135
<212> TYPE: DNA
<213> ORGANISM: Artificial
<220> FEATURE:
<223> OTHER INFORMATION: DNA sequence of a long chain peptide antigen,
      containing three types of human CD8+ T cell recognition epitope
      sequences (NY p157, MA4 p143, and WT1 p235)

<400> SEQUENCE: 31

```
ggatccatga gcctcctgat gtggattacc caatgctatt actactatta ctacaactat      60
aagagatgtt tccccgtgat ctattactac tactactatt gctatacatg gaatcagatg     120
aacctgtgag aattc                                                      135
```

<210> SEQ ID NO 32
<211> LENGTH: 135
<212> TYPE: DNA
<213> ORGANISM: Artificial
<220> FEATURE:
<223> OTHER INFORMATION: DNA sequence of a long chain peptide antigen,
      containing three types of human CD8+ T cell recognition epitope
      sequences (NY p157, MA4 p143, and WT1 p235)

<400> SEQUENCE: 32

```
ggatccatga gcctgctcat gtggatcaca caatgcacca ctactaccac aaccaactac      60
aagagatgtt tccccgtgat taccacaacc acaactacgt gctatacgtg gaatcagatg     120
aacctgtgag aattc                                                      135
```

<210> SEQ ID NO 33
<211> LENGTH: 135
<212> TYPE: DNA
<213> ORGANISM: Artificial
<220> FEATURE:
<223> OTHER INFORMATION: DNA sequence of a long chain peptide antigen,
      containing three types of human CD8+ T cell recognition epitope
      sequences (NY p157, MA4 p143, and WT1 p235)

<400> SEQUENCE: 33

```
ggatccatga gcttgctcat gtggatcacc caatgtggag gaggtggtgg aggcaactac      60
aagcgatgtt tccccgtgat aggcggtgga ggtggagggt gctacacatg gaaccagatg     120
aacctgtgag aattc                                                      135

<210> SEQ ID NO 34
<211> LENGTH: 135
<212> TYPE: DNA
<213> ORGANISM: Artificial
<220> FEATURE:
<223> OTHER INFORMATION: DNA sequence of a long chain peptide antigen,
      containing three types of human CD8+ T cell recognition epitope
      sequences (NY p157, MA4 p143, and WT1 p235)

<400> SEQUENCE: 34
ggatccatga gtctgctgat gtggatcact cagtgtcctc caccaccacc acccaactac      60
aagaggtgtt tccccgtgat tccaccacct cctcctccat gctatacctg gaatcagatg     120
aacctgtgag aattc                                                      135

<210> SEQ ID NO 35
<211> LENGTH: 7
<212> TYPE: PRT
<213> ORGANISM: Artificial
<220> FEATURE:
<223> OTHER INFORMATION: Peptide sequence containing mouse CD8+ T cell
      epitope, NY p82

<400> SEQUENCE: 35

Gly Pro Glu Ser Arg Leu Leu
1               5
```

LONG CHAIN ANTIGEN CONTAINING INTEREPITOPE SEQUENCE THAT PROMOTES ANTIGEN PRESENTATION TO T CELLS

CROSS-REFERENCE

This application is a continuation of U.S. application Ser. No. 15/026,841 filed on Apr. 1, 2016, now abandoned, which was the US national stage of International Patent Application No. PCT/JP2014/082691 filed on Dec. 10, 2014, which claims priority to Japanese Patent Application No. 2013-256900 filed on Dec. 12, 2013.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| MIE003_Seq_List2.txt | Aug. 26, 2016 | 17 |

The present invention relates to a long chain antigen containing one or more interepitope sequence(s) that promote(s) antigen presentation to T cells.

TECHNICAL FIELD

The present invention relates to a T cell inducing vaccine containing an interepitope sequence that promotes antigen presentation.

BACKGROUND ART

The importance of cell-mediated immunity in tumor rejection by a cancer host has been revealed as a result of long years of research related to immune responses against cancer. In particular, it has been revealed that $CD8^+$ killer T cells ($CD8^+$ cytotoxic T cells) are effector cells having an action of directly destroying tumors, that $CD4^+$ helper T cells are important regulatory cells that enhance the functions of $CD8^+$ killer T cells and antigen-presenting cells, and that professional antigen-presenting cells, such as dendritic cells and macrophages, stimulate T cells by presenting antigens thereto and activate T cells via costimulatory molecules, such as CD80, CD86, and cytokines, etc., and the roles and positioning of the respective cells responsible for cellular immune responses against tumors have been established as described below (Non-Patent Document 1).

Tumor cell derived proteins, after being phagocytosed by antigen-presenting cells, are cleaved into peptides of various lengths by proteasomes, proteases, and peptidases within the cells. Among the resulting peptides, peptides of 8-10 amino acids are loaded as antigen epitope peptides onto major histocompatibility complex (MHC) class I molecules and can be presented on the surfaces of the antigen-presenting cells. $CD8^+$ killer T cells use T cell receptors (TCRs) to specifically recognize the MHC class I/antigenic peptide complexes and become activated. The activated $CD8^+$ killer T cells detect MHC class I/antigenic peptide complexes that are also present on tumor cells and destroy the tumor cells using effector molecules, such as granzymes and perforin.

The function of $CD4^+$ helper T cells is important for sufficient activation of $CD8^+$ killer T cells (Non-Patent Document 2). Antigenic proteins taken up by the antigen-presenting cells are cleaved into various lengths by proteases and peptidases within the cells and among the resulting antigenic peptides, those of 15-20 amino acids form complexes with MHC class II molecules and can be presented on the antigen-presenting cells. $CD4^+$ helper T cells recognize these specifically and are activated. The activated $CD4^+$ helper T cells enhance differentiation, growth, and functions of $CD8^+$ killer T cells via secretion of cytokines, such as interferon (IFN) –γ and interleukin (IL)-2. The $CD4^+$ helper T cells also have a function of activating antigen-presenting cells via a CD40 ligand/CD40 pathway, and the antigen-presenting cells activated by the $CD4^+$ helper T cells are improved in the capability to stimulate $CD8^+$ killer T cells (Non-Patent Document 3). It is well known from before that $CD4^+$ helper T cells also have an action of enhancing antigen-specific IgG antibody production in B cells.

Based on the above understanding of T-cell immune response, a cancer vaccine therapy has been conceived where a tumor specific antigen is repeatedly administered as a vaccine antigen to induce tumor-specific $CD8^+$ killer T cells within a patient's body to suppress the growth, metastasis, and recurrence of cancer. Various forms of the antigen of the cancer vaccines are known, such as synthetic peptides, recombinant proteins, processed cells. The present inventors have previously prepared a cancer vaccine using a full-length recombinant protein of a tumor antigenic protein as the antigen. The full-length protein includes diverse antigenic peptides recognized by $CD8^+$ killer T cells and $CD4^+$ helper T cells and is expected to activate both types of T cells at the same time. However, with an exogenous (extracellular) antigenic protein, although the activation of $CD4^+$ helper T cells via the MHC class II pathway proceeds readily, the activation of $CD8^+$ killer T cells via the MHC class I pathway does not proceed readily. This is due to reasons of mechanisms of uptake and antigen processing of exogenous antigenic proteins in antigen-presenting cells (Non-Patent Document 4).

Therefore many attempts are being made in and outside Japan to chemically synthesize short chain peptides, mainly, epitope peptides of 8 to 10 residues recognized by $CD8^+$ killer T cells and clinically apply vaccines using these peptides as antigens. With short peptide antigens, presentation to T cells occurs readily because such peptides bind directly to MHC molecules on cell surfaces without undergoing uptake and antigen processing within antigen-presenting cells. Also, short chain peptides can be manufactured by chemical synthesis and has the advantage of being simpler to manufacture than recombinant proteins, which requires the use of genetically modified organisms.

However, immunological problems have been pointed out in regard to the direct binding of short peptide antigens to MHC molecules on cell surfaces without undergoing uptake and antigen processing within antigen-presenting cells (Non-Patent Document 5). Exogenous antigenic proteins are phagocytosed by professional antigen-presenting cells, such as dendritic cells and macrophages, that are provided with costimulatory molecules (CD80, CD86, etc.) and are processed within the cells, and antigen presentation to T cells is performed in a mode with appropriate concentration and costimulation. On the other hand, short peptide antigens bind directly to MHC molecules on cell surfaces and therefore even general somatic cells, which do not have uptake ability (phagocytic ability) and do not express costimulatory molecules, can present the short peptide antigens in a massive, inappropriate mode that lacks costimulation. In this case, the T cells that recognize the complexes of the short peptide antigens and MHCs become prone to depletion and apoptosis and this can consequently lead to immunological tolerance to the targeted antigen.

In view of such problems of short chain peptide vaccines, the usefulness of long chain synthetic peptide antigens is attracting attention (Non-Patent Document 5). A long chain peptide antigen is a polypeptide having several dozen residues such that include two or more T cell recognition epitope peptides. Unlike a short chain peptide, a long chain peptide antigen cannot bind directly in intact form to an MHC molecule. As with protein antigens, long chain peptide antigens undergo uptake and intracellular processing by professional antigen-presenting cells with phagocytic ability, such as dendritic cells and macrophages, and the T cell epitope peptides included in the long chain peptide antigens form complexes with MHC molecules only thereafter and are thus presented to T cells in a mode with appropriate concentration and costimulation. Long chain peptide antigens do not function as vaccine antigens with general somatic cells lacking antigen phagocytic ability and therefore, unlike short chain peptide vaccines, do not give rise to inappropriate antigen presentation to T cells. Moreover, chemical synthetic methods can be used to manufacture long chain peptide antigens and therefore, as with short peptide antigens, the advantage of being comparatively easy to manufacture is also provided.

Long chain peptide antigens manufactured by chemical synthesis also have a major advantage in that it is possible to freely design the sequence. A long chain peptide antigen is designed so that two or more T cell epitopes are included within a single peptide, and these T cell epitopes may be derived from a single cancer antigenic protein or may be derived from a plurality of cancer antigenic proteins. Also, the T cell epitopes may be restrictive to a single MHC or may be restrictive to a plurality of MHCs. It is also possible to design so that a long chain peptide antigen includes an epitope recognized by a CD8$^+$ killer T cell and an epitope recognized by a CD4$^+$ helper T cell at the same time. Long chain peptide antigens can thus serve as high performance vaccine antigens that can induce diverse T cells. However, for the set of epitopes contained in a long chain peptide antigen to be presented to T cells efficiently, the epitopes must be cut out as epitope peptides of lengths and sequences enabling binding with MHC molecules by sequences between the respective epitopes on the long chain peptide antigen being cleaved appropriately by proteasomes, proteases, and peptidases in an antigen-presenting cell based on the mechanism of antigen presentation reactions.

In regard to MHC class II binding epitope peptides recognized by CD4$^+$ helper T cells, the terminuses of the epitope peptide binding groove on an MHC class II molecule are in an open state and epitope peptides of various lengths can bind to the MHC class II molecule (Non-Patent Document 6). Therefore, with MHC class II binding epitope peptides, the restriction of length is comparatively relaxed. On the other hand, in regard to MHC class I binding epitope peptides recognized by CD8$^+$ killer T cells, the terminuses of the epitope peptide binding groove on an MHC class I molecule are in a closed state and only epitope peptides, strictly restricted to 8 to 10 residues, can bind to the MHC class I molecule. It is thus especially important with MHC class I binding epitope peptides that peptides of appropriate lengths are produced in antigen-presenting cells.

The lengths and sequences of the epitope peptides that bind to MHC molecules are determined by complex cleavage reactions involving intracellular proteasomes and various proteases and peptidases. In the production of MHC class I binding epitope peptides, proteasomes present in the cytoplasm first perform rough cleavage of the antigenic protein or long chain peptide antigen. The terminuses of the resulting peptide fragments are cleaved by other proteases and peptidases based on certain substrate sequence specificities and trimmed to appropriate lengths (trimming reactions). Although a group of enzymes that trim the N-terminuses of the peptide fragments in this process exists, enzymes that trim the C-terminuses are unknown, and determination of the C-terminuses of the MHC class I binding epitope peptides is dependent only on the initial cleavage reactions by the proteasomes (Non-Patent Document 7). However, the substrate sequence specificities of proteasomes have not been revealed in detail and it is difficult to predict peptide sequences that can be cleaved readily by proteasomes.

In view of the above epitope production mechanism, how the sequences between the epitopes included in the long chain peptide antigen are cleaved by the intracellular proteasomes, proteases, and peptidases strongly influences the production of the preceding and subsequent epitope peptides and is consequently considered to be an extremely important factor that defines the induction of T cells by vaccines using long chain peptide antigens.

PRIOR ART DOCUMENTS

Non-Patent Documents

Non-Patent Document 1: Ribas, A., et al., Clin. Oncol. 2003; 21(12): 2415-2432

Non-Patent Document 2: Shiku, H., Int. J. Hematol. 2003; 77(5): 435-8.

Non-Patent Document 3: Behrens, G., et al., Immunol. Cell Biol. 2004; 82(1): 84-90

Non-Patent Document 4: Shen, L. & Rock, K. L., Curr. Opin. Immunol. 2006; 18(1): 85-91

Non-Patent Document 5: Melief, C. J. M., & van der Burg, S. H., Nature Rev. Cancer, 2008; 8(5): 351-360.

Non-Patent Document 6: Holland, C. J., et al., Front Immunol. 2013; 4: 172.

Non-Patent Document 7: Goldberg, A. L., et al., Mol. Immunol. 2002; 39 (3-4): 147-64.

Non-Patent Document 8: Muraoka, D., et al., Vaccine. 2013; 31: 2110-2118.

SUMMARY OF THE INVENTION

For the T cell epitope peptides included in a certain long chain peptide or protein to be efficiently presented as antigens, the epitope peptide sequences must be cut out appropriately from the long chain peptide or protein by intracellular proteasomes, proteases, and peptidases. For this purpose, it is necessary for the sequences between the epitopes to aptly include recognition sites for the proteasomes, proteases, and peptidases.

In conventional arts, it was hardly examined what sort of interepitope sequence would satisfy the above condition. Therefore, with a vaccine using a long chain peptide antigen designed without examining the interepitope sequence, the induction of T cells that recognize the included epitope peptides is weak or cannot be confirmed in some cases.

The present invention has been made in view of the circumstances described above, and an object thereof is to provide, in a long chain peptide antigen containing a plurality of epitope peptides, an interepitope sequence that effectively achieves antigen presentation of the respective epitope peptides.

In a long chain peptide antigen having a plurality of epitopes according to the present teachings, each interepitope sequence is selected from a group consisting of two to ten consecutive tyrosines, two to ten consecutive threonines, two to ten consecutive alanines, two to ten consecutive histidines, two to ten consecutive glutamines, and two to ten consecutive asparagines and it is especially preferable for the sequence to be tyrosines, glutamines, or asparagines. Here, the number of consecutive tyrosines, consecutive threonines, consecutive histidines, consecutive glutamines, or consecutive asparagines may be four to eight, or four to six, or six.

By having the above arrangement, the long chain peptide antigen is cleaved inside a body (host) by host enzymes so that the respective epitopes can undergo antigen presentation and the respective epitopes thus exhibit antigen presenting abilities effectively. Also, in a long chain peptide antigen having an interepitope sequence constituted of consecutive tyrosines, uptake into antigen-presenting cells is also improved.

The above-described long chain peptide antigen may be used in anticancer vaccines (including dendritic cell vaccines), antibacterial vaccines, and antiviral vaccines.

Also, such vaccines may be peptide vaccines, DNA vaccines, mRNA vaccines, and dendritic cell vaccines. In the case of a dendritic cell vaccine, a peptide antigen or mRNA is added.

Also the long chain peptide antigen may be administered in combination with a hydrophobized polysaccharide, especially, cholesterol-modified pullulan (CHP) as a delivery system.

DETAILED DESCRIPTION

Figure 1:
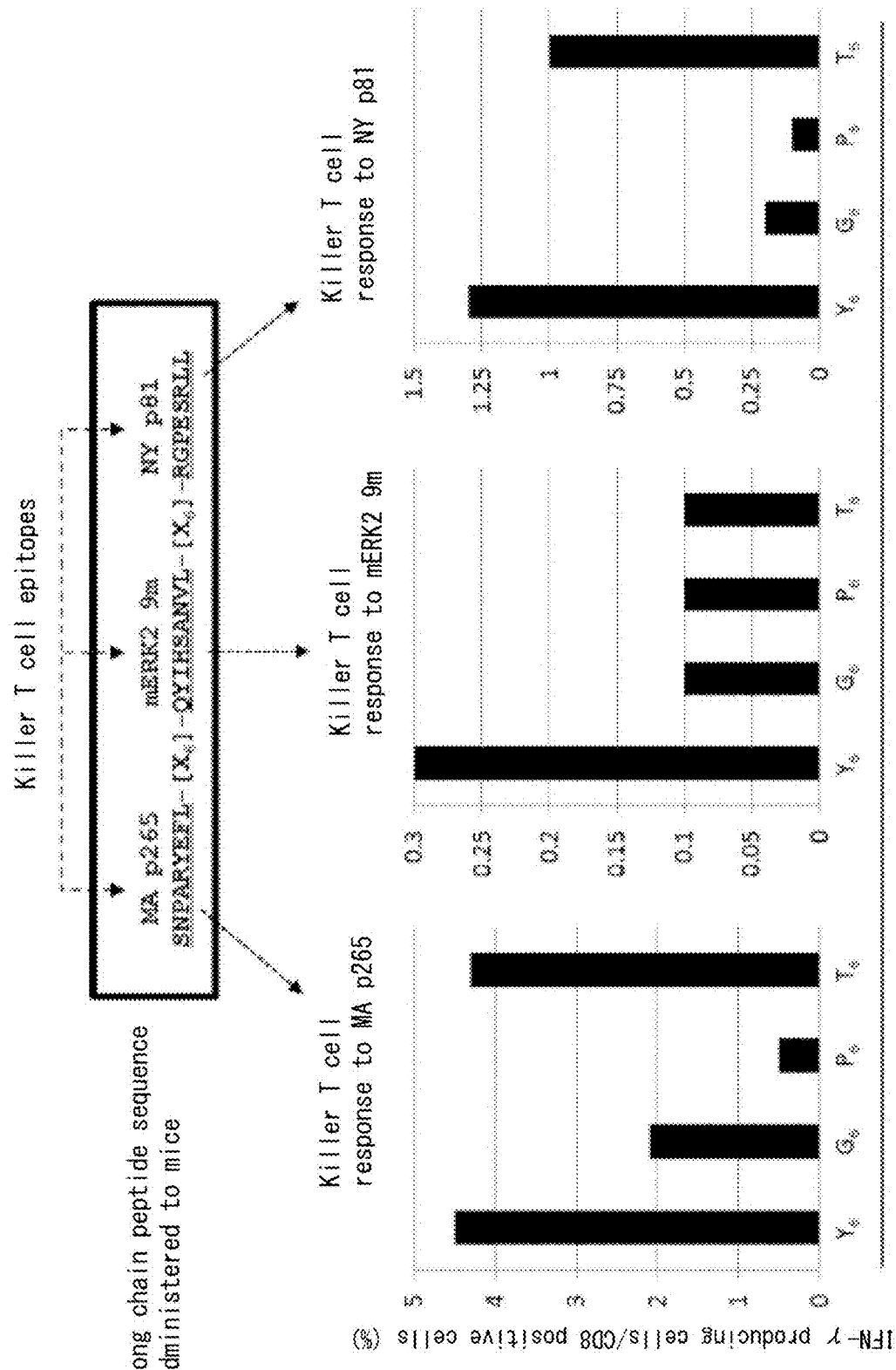
FIG. 1 shows the influences of differences in interepitope sequences of long chain peptide vaccines, containing a plurality of CD8+ T cell epitopes, on specific CD8+ T cell induction by the vaccines were examined. Long chain peptide antigens MEN, all containing three types of mouse CD8+ T cell epitope sequences (MA p265 (Sequence No. 27), NY p81 (Sequence No. 29), and mERK2 9m (Sequence No. 28)), were synthesized. The interepitope sequences between the respective epitopes were respectively six consecutive tyrosines (Y6) (Sequence No. 1), six consecutive glycines (G6) (Sequence No. 2), six consecutive prolines (P6) (Sequence No. 3), or six consecutive threonines (T6) (Sequence No. 4). Each long chain peptide antigen was complexed with cholesterol-modified pullulan (CHP), which is a type of delivery system, and administered as a vaccine to a mouse. In the process of administration, CpG oligo DNA was coadministered as an adjuvant. Spleen cells were collected one week after the final administration and the frequencies of CD8+ T cells specific to the respective epitope sequences were measured by an intracellular cytokine staining method.

Although embodiments of the present invention shall be described with reference to the drawings, the technical scope of the present invention is not restricted to these embodiments and the invention may be carried out in various modes without changing the gist of the invention. Also, the technical scope of the present invention extends to the range of equivalents.

<Materials and Methods>

(1) Test Animals

Six- to twelve-week-old female BALB/c mice were purchased from Japan SLC, Inc. and reared at the Animal Center of Mie University Faculty of Medicine. The animal experiment protocol was approved by the Ethics Committee of Mie University Faculty of Medicine.

(2) Peptides

Synthetic long chain peptides were purchased from Bio-Synthesis Inc. The sequences of the synthetic long chain peptides were as follows.

```
MEN(Y₆):
                                          (Sequence No. 1)
SNPARYEFLYYYYYYQYIHSANVLYYYYYYRGPESRLL MEN(G₆):
                                          (Sequence No. 2)
SNPARYEFLGGGGGGQYIHSANVLGGGGGGRGPESRLL MEN(P₆):
                                          (Sequence No. 3)
SNPARYEFLPPPPPPQYIHSANVLPPPPPPRGPESRLL
```

```
MEN(T₆):
                                (Sequence No. 4)
SNPARYEFLTTTTTTQYIHSANVLTTTTTTRGPESRLL NME(Y₆):
                                (Sequence No. 5)
RGPESRLLYYYYYYSNPARYEFLYYYYYYQYIHSANVL NME(G₆):
                                (Sequence No. 6)
RGPESRLLGGGGGGSNPARYEFLGGGGGGQYIHSANVL NME(P₆):
                                (Sequence No. 7)
RGPESRLLPPPPPPSNPARYEFLPPPPPPQYIHSANVL ENM(Y₆):
                                (Sequence No. 8)
QYIHSANVLYYYYYYRGPESRLLYYYYYYSNPARYEFL MEN(Y₁):
                                (Sequence No. 9)
SNPARYEFLYQYIHSANVLYRGPESRLL MEN(Y₂):
                                (Sequence No. 10)
SNPARYEFLYYQYIHSANVLYYRGPESRLL MEN(Y₃):
                                (Sequence No. 11)
SNPARYEFLYYYQYIHSANVLYYYRGPESRLL MEN(Y₄):
                                (Sequence No. 12)
SNPARYEFLYYYYQYIHSANVLYYYYRGPESRLL MEN(Y₅):
                                (Sequence No. 13)
SNPARYEFLYYYYYQYIHSANVLYYYYYRGPESRLL MEN(Y₈):
                                (Sequence No. 14)
SNPARYEFLYYYYYYYYQYIHSANVLYYYYYYYYRGPESRLL MEN(Y₁₀):
                                (Sequence No. 15)
SNPARYEFLYYYYYYYYYYQYIHSANVLYYYYYYYYYYRGPESRLL ESO1 LP (native type):
                                (Sequence No. 16)
GARGPESRLLEFYLAMPFATPMEAELARRSLAQDAPPLPV ESO1 LP (Y₆):
                                (Sequence No. 17)
GPESRLLYYYYYYYLAMPFATPMEAELARRSLA NMW(A₆):
                                (Sequence No. 18)
SLLMWITQCAAAAAANYKRCFPVIAAAAAACMTWNQMNL NMW(E₆):
                                (Sequence No. 19)
SLLMWITQCEEEEEENYKRCFPVIEEEEEECMTWNQMNL NMW(G₆):
                                (Sequence No. 20)
SLLMWITQCGGGGGGNYKRCFPVIGGGGGGCMTWNQMNL NMW(H₆):
                                (Sequence No. 21)
SLLMWITQCHHHHHHNYKRCFPVIHHHHHHCMTWNQMNL NMW(N₆):
                                (Sequence No. 22)
SLLMWITQCNNNNNNNYKRCFPVINNNNNNCMTWNQML NMW(P₆):
                                (Sequence No. 23)
SLLMWITQCPPPPPPNYKRCFPVIPPPPPPCMTWNQMNL NMW(Q₆):
                                (Sequence No. 24)
SLLMWITQCQQQQQQNYKRCFPVIQQQQQQCMTWNQMNL NMW(S₆):
                                (Sequence No. 25)
SLLMWITQCSSSSSSNYKRCFPVISSSSSSCMTWNQMNL NMW(Y₆):
                                (Sequence No. 26)
SLLMWITQCYYYYYYNYKRCFPVIYYYYYYCMTWNQMNL
```

Synthetic short chain peptides were purchased from Sigma Genosys. The amino acid sequences of the peptides were as follows.

```
                                (Sequence No. 27)
           MA p265: SNPARYEFL (Sequence No. 28)
          mERK2 9m: QYIHSANVL (Sequence No. 29)
           NY p81: RGPESRLL (Sequence No. 30)
          NY p157: SLLMWITQC
```

Template cDNAs used to synthesize the RNA vaccines were purchased from Operon Biotechnologies, Inc. The sequences of the cDNAs were as follows.

```
NMW(Y₆):
                                (Sequence No. 31)
GGATCCATGAGCCTCCTGATGTGGATTACCCAATGCTATTACTACTATTA

CTACAACTATAAGAGATGTTT CCCCGTGATCTATTACTACTACTAT

TGCTATACATGGAATCAGATGAACCTGTGAGAATTC

NMW(T₆):
                                (Sequence No. 32)
GGATCCATGAGCCTGCTCATGTGGATCACACAATGCACCACTACTACCAC

AACCAACTACAAGAGATGT TTCCCCGTGATTACCACAACCACAACTACG

TGCTATACGTGGAATCAGATGAACCTGTGAGAATTC

NMW(G₆):
                                (Sequence No. 33)
GGATCCATGAGCTTGCTCATGTGGATCACCCAATGTGGAGGAGGTGGTGG

AGGCAACTACAAGCGATGTTTCCCCGTGATAGGCGGTGGAGGTGGAGGGT

GCTACACATGGACCAGATGACCTGTGAGATTC

NMW(P₆):
                                (Sequence No. 34)
GGATCCATGAGTCTGCTGATGTGGATCACTCAGTGTCCTCCACCACCACC

ACCCAACTACAAGAGGTGT TTCCCCGTGATTCCACCACCTCCTCCTCCA

TGCTATACCTGGAATCAGATGAACCTGTGAGAATTC
```

(3) Other Reagents

Cholesterol-modified pullulan (abbreviation CHP) (CHP-80T) was obtained from NOF Corporation. CpG oligo DNA was purchased from Hokkaido System Science Co., Ltd. FITC-labeled anti-CD4 monoclonal antibody (clone RM4-5), PerCP-Cy5.5-labeled anti-CD8 monoclonal antibody (clone 53-6.7), and APC-labeled anti-IFN-γ antibody (clone XMG1.2) were purchased from eBiosciece Inc. or BD Biosciences. Anti-human IFN-γ antibody and biotinylated anti-human IFN-γ antibody was purchased from Mabtech AB.

(4) Preparation of Complexes of Long Chain Peptide Antigens and CHP

Each long chain peptide was dissolved in dimethyl sulfoxide (DMSO) at a concentration of 10 mg/mL. CHP was dissolved in 6 M urea-containing phosphate buffered saline (PBS) at a concentration of 10 mg/mL 1 mL (10 mg) of the long chain peptide solution and 20 mL (200 mg) of the CHP solution were mixed and left to stand at room temperature overnight in a dark place. The liquid mixture was transferred into a dialysis membrane (molecular weight cutoff: 3,500; Thermo Fisher Scientific, Inc.) and dialyzed for 2 hours to overnight at 4° C. against 0.6 M urea-containing PBS of a volume ratio of not less than 100 times as the dialysis outer solution. Dialysis was then performed for 2 hours to overnight at 4° C. against 0.06 M urea-containing PBS of a volume ratio of not less than 100 times as the dialysis outer solution. Dialysis was performed again for 2 hours to overnight at 4° C. against PBS of a volume ratio of not less than 100 times as the dialysis outer solution. The dialyzed inner solution was collected, filtered through a filtration sterilization filter of 0.45 μm or 0.22 μm pore size, and thereafter the UV absorption at 280 nm was measured to determine the final concentration of the long chain peptide from its molecular extinction coefficient.

(5) Administration of Vaccines to Mice and Separation of Spleen Cells

Each CHP/long chain peptide complex as the vaccine and the CpG oligo DNA as the adjuvant were administered at the same time to a mouse. Administration was performed by subcutaneous injection on the back of the mouse. As the dose, the CHP/long chain peptide complex was administered at 0.05 to 0.1 mg equivalent of long chain peptide per administration. The CpG oligo DNA was administered at 0.05 mg per administration. One week after the final administration, spleen cells were separated by the following procedure from each vaccine-administered mouse. The spleen was isolated from the mouse and removed of blood by rinsing with RPMI1640 medium. After the spleen was triturated using a glass slide, the released cells were collected in RPMI1640 medium. After centrifuging (400×g, 5 minutes, 4° C.), the supernatant was removed and the cells were treated for 1 minute by adding 2 mL of ACK solution. 18 mL of RPMI1640 medium were added and centrifugation (400×g, 5 minutes, 4° C.) was performed. The supernatant was removed and the cells were suspended in RPMI1640 medium of an appropriate amount. After counting the number of cells, the cells were suspended in RPMI1640 medium containing 10% fetal bovine serum (FBS) so that the cell concentration was $1\times10^7$ cells/mL.

(6) Intracellular Cytokine Staining of Mouse Spleen Cells

The mouse spleen cells were added at $5\times10^6$ cells/0.5 mL per well to a 24-well culture plate (Nunc). NY p81, MAGE p265, or mERK2 9m as the short chain peptide for CD8$^+$ T cell stimulation or ESO1 LP (native type) or ESO1 LP ($Y_6$) CD4$^+$ T cell stimulation was added at a concentration of 10 μM and culturing under 37° C. and 5% $CO_2$ was performed for 6 hours. Thereafter, GoldiPlug (BD Biosciences), diluted 10-fold with 10% FBS-containing RPMI1640 medium, was added at 50 μL per well and culturing under 37° C. and 5% $CO_2$ was performed for 6 hours. The cells were collected and transferred to a 96-well round bottom microplate (Nunc). After centrifuging (1200 rpm, 1 minute, 4° C.) and removing the supernatant, the cells were suspended in 50 μL of staining buffer (PBS containing 0.5% bovine serum albumin) per well. The FITC-labeled anti-CD8 antibody or the FITC-labeled anti-CD4 antibody was added and after mixing, the cells were left to stand for 15 minutes in a dark place at 4° C. After rinsing the cells twice with 200 μL of the staining buffer, 100 μL of Cytofix/Cytoperm buffer (BD Biosciences) were added and mixed gently. After leaving to stand for 20 minutes in a dark place at room temperature, rinsing with 100 μL of Perm/Wash buffer (BD Biosciences) was performed twice. 50 μL of Perm/Wash buffer with the respective types of anti-cytokine antibodies added were added to the cells and after suspending gently, the cells were left to stand for 15 minutes in a dark place at room temperature. After rinsing twice with 100 μL of Perm/Wash buffer, the cells were re-suspended in 200 μL of the staining buffer and transferred to a round-bottom polystyrene tube (BD Biosciences). The cells were analyzed by a flow cytometer (FACS Canto II, BD Biosciences) using the included analysis software (FACSDiva).

(7) Mouse Tumor Growth Test

A subcloned CMS5a cell line, obtained from a CMS5 cell line isolated from fibrosarcoma induced by administering 3-methylcholanthrene to a BALB/c mouse, expresses mutant ERK2 (mERK2) as a tumor antigen and presents a CD8$^+$ T cell epitope derived from the mERK2. The CMS5a cell line cultured in a T75 flask (Nunc) was detached using PBS containing 0.5% trypsin and collected in RPMI1640 medium containing 10% FBS. After centrifuging (400×g, 5 minutes, 4° C.), the supernatant was removed, and the cells were rinsed twice with RPMI1640 medium, thereafter suspended in RPMI1640 medium at a concentration of $1\times10^6$ cells/100 μL, and implanted subcutaneously in BALB/c mice at a dose of 100 μL/individual. The CHP/long chain peptide complexes and the adjuvant were administered 7 days before tumor implantation (prophylactic condition). After tumor implantation, the length and breadth of the tumor were measured and the product thereof was recorded as tumor size. The data in the tumor growth test were compared by Student's t test using Microsoft® Excel® (Microsoft Corporation).

(8) Uptake of Long Chain Peptide Antigens by Antigen Presenting Cells

In vitro uptake of the long chain peptide antigens by antigen-presenting cells was measured as follows. Each long chain peptide labeled with a fluorescent dye was complexed with CHP by the method described above. Spleen cells separated from a normal mouse were added at $1\times10^6$ cells/0.5 mL/well to a 24-well plate. Each CHP/fluorescent-labeled long chain peptide complex was added at a concentration of 10 μg/mL and culturing was performed at 37° C. Cells were collected after 60 minutes and stained with an anti-CD11c antibody and an anti-F4/80 antibody. The uptake of the fluorescence-labeled long chain peptide antigens by CD11c$^+$ cells (dendritic cells) and F4/80$^+$ cells (macrophages) were observed using flow cytometry.

A test of uptake of long chain peptide antigens by antigen-presenting cells in individual animals was performed as follows. Each long chain peptide was fluorescence-labeled, complexed with a CHP nanogel, administered subcutaneously to BALB/c mice. 16 hours after administration, cells were collected from lymph nodes and after staining with the anti-CD11c antibody and the anti-F4/80 antibody, the uptake of the fluorescence-labeled long chain peptide antigens by CD11c$^+$ cells (dendritic cells) and F4/80$^+$ cells (macrophages) was analyzed by flow cytometry.

(9) Administration of Long Chain Peptide Vaccines to Immortalized B Cell Line (LCL)

Cryostored LCL was rinsed with RPMI medium and suspended at $1.25\times10^6$/mL in X-VIVO15 medium. This was dispensed in 0.4 mL aliquots into polypropylene tubes, and 0.1 mL of a vaccine solution (0.1 mg/mL as peptide) was added to each tube. The cells were cultured for 24 hours at 37° C. in the presence of 5% $CO_2$ and then used as antigen-presenting cells.

(10) Administration of RNA Vaccines to Immortalized B Cell Line (LCL)

mRNA was introduced by an electroporation method (300V, 700 μs) using ECM830 into LCL that was rinsed and suspended in the same manner as in (9). The cells were cultured for 24 hours at 37° C. in the presence of 5% $CO_2$ and then used as antigen-presenting cells.

(11) ELISPOT Method

75 μL aliquots of anti-IFN-γ antibody for capture, diluted to an appropriate concentration, were dispensed into a 96-well plate (Millipore Corp., Multiscreen HA, MAHAS4510) specially designed for ELISPOT and left to stand overnight at 4° C. After discarding the liquid and rinsing with RPMI medium, 100 μL aliquots of RPMI medium containing 10% fetal bovine serum were dispensed and the plate was left to stand for not less than 1 hour at 37° C. The liquid was discarded, and the LCL prepared in (9) or (10) was adjusted to $5 \times 10^4$ cells/100 μL/well and added to each well. The cryostored CD8$^+$ T cell clones were thawed, rinsed, adjusted to $5 \times 10^5$/mL with RPMI medium, and thereafter added in 0.1 mL aliquots to each well. After culturing for 24 hours at 37° C. in the presence of 5% $CO_2$, the liquid was discarded and the plate was rinsed well with phosphate buffered saline containing 0.05% Tween 20 (PBS-T). A biotin-labeled IFN-γ antibody for detection was diluted to an appropriate concentration and dispensed in 0.1 mL aliquots into each well. After letting stand overnight at 4° C., the plate was rinsed well with PBS-T, and an alkaline phosphatase-labeled streptavidin diluted to an appropriate concentration was added in 0.1 mL aliquots. After incubating for 1 hour at room temperature, the plate was rinsed well with PBS-T. A coloring solution was added in 0.1 mL aliquots and allowed to react for 5 minutes to 30 minutes at room temperature. When the formation of spots was observed, the reaction was stopped by rinsing with water.

(12) Preparation of mRNAs Encoding Long Chain Peptide Antigens cDNAs encoding the intended long chain peptide antigens were purchased as synthetic genes from Operon Biotechnologies, Inc. Each of these was cloned into the multiple cloning site of a pcDNA3.1 vector. The priming site on the T7 promoter contained in the pcDNA3.1 was used to synthesize mRNA by a conventional method using MEGAscript (registered trademark) T7 Transcription Kit, made by Life Technologies, Inc., etc.

<Test Results>

FIG. 1 shows that with vaccines having a long chain peptide, which contains a plurality of T cell epitopes, as an antigen, differences in interepitope sequence influence the success or failure of specific T cell induction by the respective epitopes. The long chain peptide antigens MEN, all containing the three types of mouse CD8$^+$ T cell epitope sequences, MA p265, NY p81, and mERK2 9m, which are derived from the human tumor antigens MAGE-A4 and NY-ESO-1 and the mouse tumor antigen, mutant ERK2 (mERK2), were synthesized. The sequence between the three types of epitopes was set to one of six consecutive tyrosines ($Y_6$), glycines ($G_6$), prolines ($P_6$), or threonines ($T_6$). Each long chain peptide antigen was complexed with cholesterol-modified pullulan (CHP), which is a type of delivery system, and administered as a vaccine to a mouse. With the long chain peptide vaccine adopting $Y_6$ or $T_6$ as the interepitope sequence, specific CD8$^+$ T cells corresponding to all three types of epitopes were clearly induced. On the other hand, with the vaccine using $G_6$ or $P_6$ as the interepitope sequence, the induction of specific CD8$^+$ T cells corresponding to all three types of epitopes was clearly weak. From this, it was revealed that the interepitope sequence strongly influences T cell induction by the preceding and subsequent epitopes and that consecutive tyrosines or threonines is preferable as the interepitope sequence.

Figure 2:
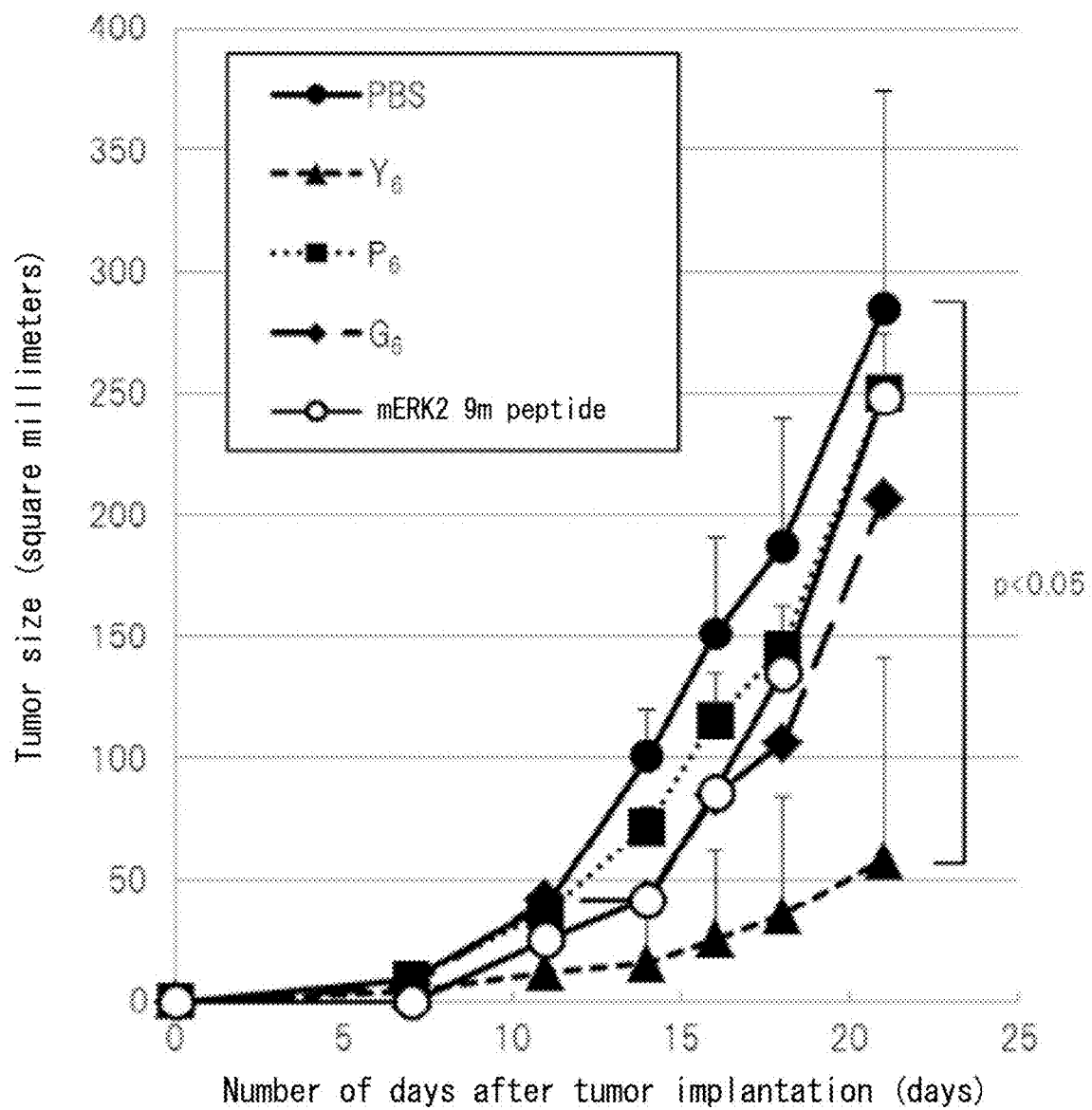
FIG. 2 shows the influences of differences in the interepitope sequences of long chain peptide vaccines, containing a plurality of CD8+ T cell epitopes, on the therapeutic effects of the vaccines were examined. Long chain peptide antigens MEN, all containing three types of mouse CD8+ T cell epitope sequences (MA p265 (Sequence No. 27), NY p81 (Sequence No. 29), and mERK2 9m (Sequence No. 28)), were synthesized. The interepitope sequences between the respective epitopes were respectively six consecutive tyrosines (Y6) (Sequence No. 1), six consecutive glycines (G6) (Sequence No. 2), or six consecutive prolines (P6) (Sequence No. 3). Each long chain peptide antigen was complexed with CHP and administered in a single dose as a vaccine to a mouse. As a control, a short chain peptide vaccine, constituted of just the mERK2 9m peptide, was mixed with Freund's incomplete adjuvant and administered. In the process of administration, CpG oligo DNA was coadministered as an adjuvant. On the day after administration, a mouse fibrosarcoma cell line CMS5a, expressing mERK2 as a tumor antigen and presenting the CD8+ T cell epitope mERK2 9m derived from the same antigen, was implanted subcutaneously and its growth was recorded over time.

The influences of differences in interepitope sequence of long chain peptide antigens on antitumor effects of vaccines were examined using a mouse tumor implant model (FIG. 2). The long chain peptide antigens MEN, all containing three types of mouse CD8$^+$ T cell epitope sequences (MA p265, NY p81, and mERK2 9m), were synthesized, and the sequence between the respective epitopes was set to one of six consecutive tyrosines ($Y_6$) glycines ($G_6$), or prolines ($P_6$). Each long chain peptide antigen was complexed with CHP and administered in a single dose as a vaccine to a mouse. As a control, a short chain peptide vaccine, constituted of just the mERK2 9m peptide, was administered. On the day after administration, the mouse fibrosarcoma cell line CMS5a, presenting the CD8$^+$ T cell epitope mERK2 9m derived from the mERK2 antigen, was implanted subcutaneously and its growth was recorded over time. With the vaccine using the long chain peptide antigen MEN ($Y_6$), the growth of the tumor was suppressed significantly ($p<0.05$). In comparison, the vaccine using MEN ($G_6$) or MEN ($P_6$) or the mERK2 9m short chain peptide vaccine, significant suppression of tumor growth was not observed. It is believed that the differences in specific CD8$^+$ killer T cell induction resulting from the differences interepitope sequence seen in FIG. 1 significantly influenced the therapeutic effect due to the vaccines. It was also revealed that when an optimal interepitope sequence is adopted, a long chain peptide vaccine exhibits a therapeutic effect that outperforms a short chain peptide vaccine (in the present case, the vaccine having the mERK2 9m peptide as the antigen).

Figure 3:
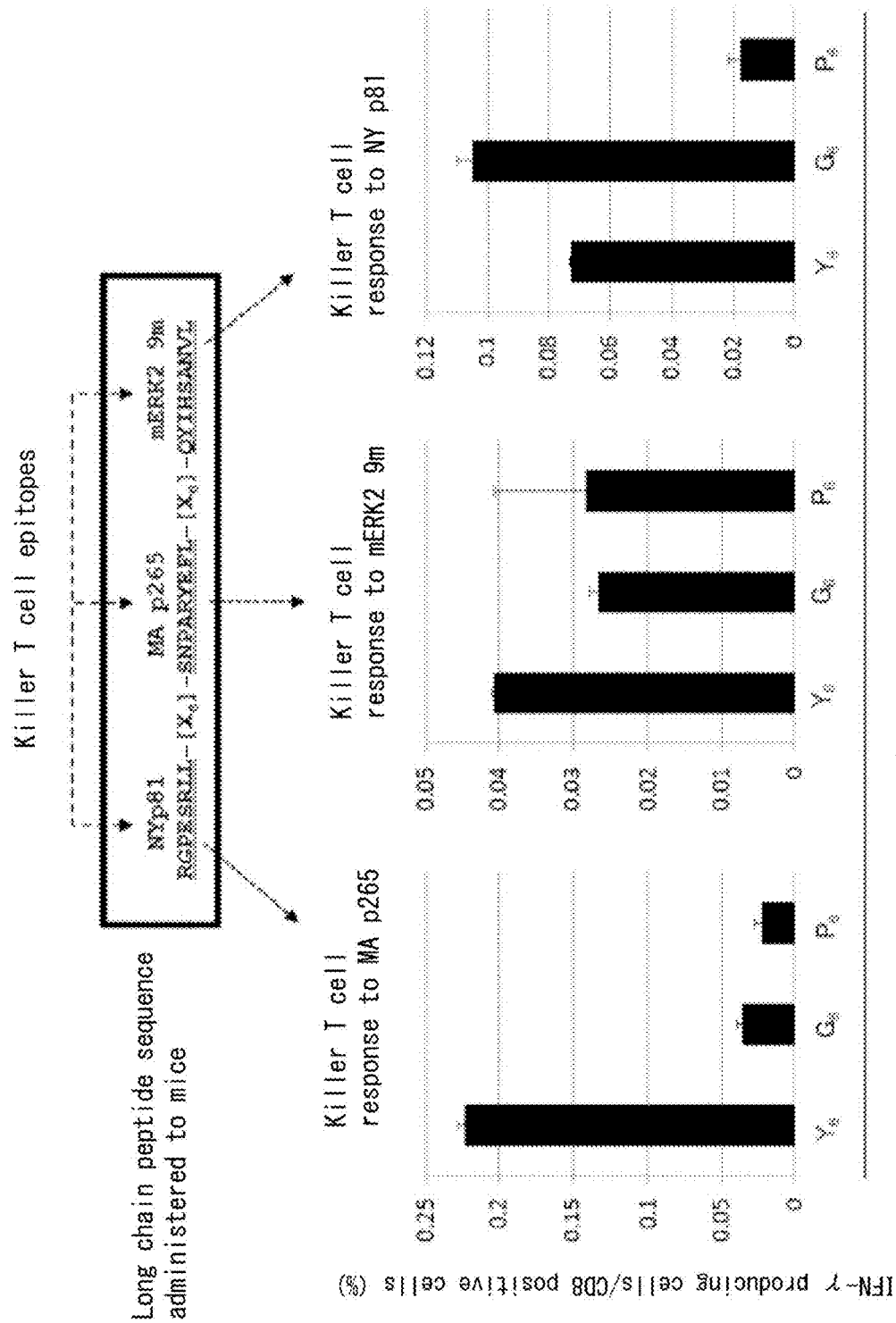
FIG. 3 shows the influences of differences in the interepitope sequences of long chain peptide vaccines, containing a plurality of CD8+ T cell epitopes, on specific CD8+ T cell induction by the vaccines were examined. Long chain peptide antigens NME, all containing three types of mouse CD8+ T cell epitope sequences (MA p265 (Sequence No. 27), NY p81 (Sequence No. 29), and mERK2 9m (Sequence No. 28)), were synthesized. The antigens differ from the MEN sequences shown in FIG. 1 in the order of the three types of epitopes. The interepitope sequences between the respective epitopes were respectively six consecutive tyrosines (Y6) (Sequence No. 5), six consecutive glycines (G6) (Sequence No. 6), or six consecutive prolines (P6) (Sequence No. 7). Vaccines containing the respective long chain peptide antigens were administered to mice in the same manner as in FIG. 1 and the frequencies of CD8+ T cells specific to the respective epitope sequences were measured by the intracellular cytokine staining method.
Figure 4:
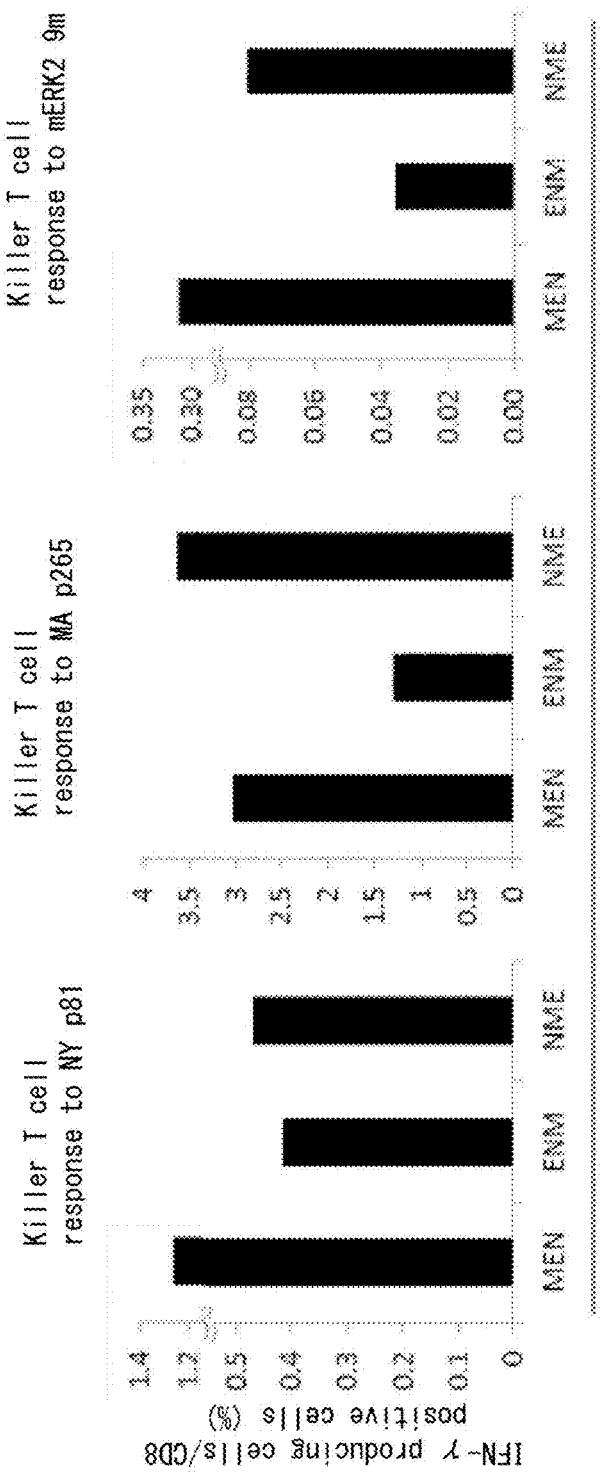
FIG. 4 shows whether or not the usefulness (effectiveness) of an interepitope sequence, constituted of consecutive tyrosines, is influenced by preceding and subsequent epitope sequences was examined. Long chain peptide antigens MEN, ENM, and NME, all containing three types of mouse CD8+ T cell epitope sequences (MA p265 (Sequence No. 27), NY p81 (Sequence No. 29), and mERK2 9m (Sequence No. 28)), were synthesized. MEN, ENM, and MEN differ in the order of the three types of epitopes. The interepitope sequences between the respective epitopes were each six consecutive tyrosines (Y6) (Sequence Nos. 1, 5 and 8). Vaccines containing the respective long chain peptide antigens were administered to mice in the same manner as in FIG. 1 and the frequencies of CD8+ T cells specific to the respective epitope sequences were measured by the intracellular cytokine staining method.

The usefulness of the consecutive tyrosine sequence as an interepitope sequence when the order of epitopes on the long chain peptide antigen differs from that in the case of FIG. 1, that is, when the epitope sequences preceding and subsequent the interepitope sequence differ was examined. The long chain peptide antigens NME, all containing three types of mouse CD8$^+$ T cell epitope sequences (MA p265, NY p81, and mERK2 9m), were synthesized. The NME differ from the MEN in FIG. 1 in the order of the three types of epitopes. The sequence between the respective epitopes was set to one of six consecutive tyrosines ($Y_6$), glycines ($G_6$), or prolines ($P_6$). When vaccines containing the respective long chain peptide antigens were administered to mice, specific CD8$^+$ T cells corresponding to all three types of epitopes were clearly induced with the vaccine using $Y_6$ as the interepitope sequence in the same manner as in FIG. 1 (FIG. 3). On the other hand, with the vaccine using $G_6$ or $P_6$, specific CD8$^+$ T cell induction was not observed for one or two types of epitopes among the three types of epitopes. To further examine the influence of the epitope sequences preceding and subsequent the interepitope sequence, the long chain peptide antigens MEN, ENM, and NME, which are changed in the order of the three types of epitope sequences (MA p265, NY p81, and mERK2 9m) but with which the interepitope sequence is fixed at six consecutive tyrosines ($Y_6$), were prepared. When vaccines containing the respective long chain peptide antigens were administered to mice, specific CD8$^+$ T cells corresponding to all three types of epitopes were clearly induced with all of the long chain peptide antigens (FIG. 4). It was thus revealed that with a long chain peptide antigen containing the interepitope sequence constituted of consecutive tyrosines, specific CD8+ T cells for all epitopes can be induced regardless of the sequences preceding and subsequent the interepitope sequence.

Figure 5:
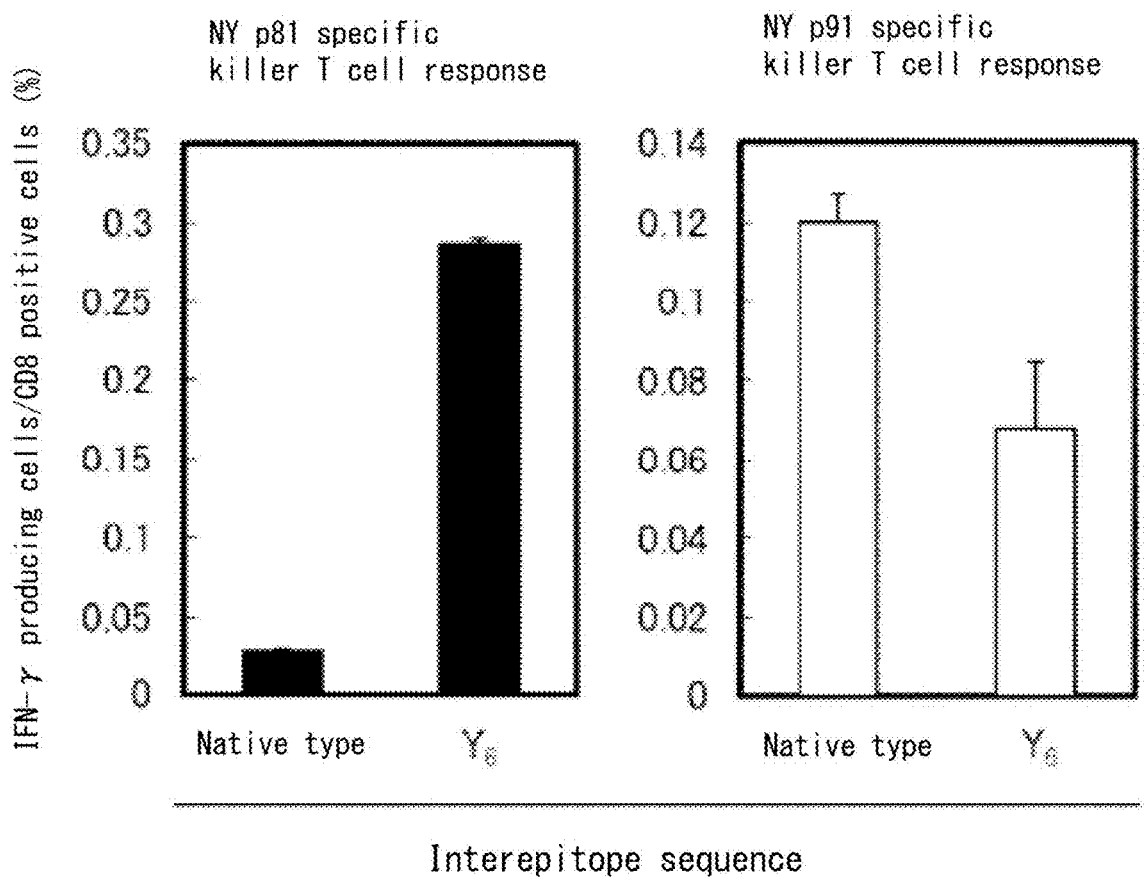
FIG. 5 shows the influences of the difference between a native sequence and a consecutive tyrosine sequence as the interepitope sequence on specific CD8+ T cell induction and specific CD4+ T cell induction by vaccines were examined. A long chain peptide antigen ESO1 LP (native type) (Sequence No. 16) and a long chain peptide antigen ESO1 LP (Y6) (Sequence No. 17), both containing a mouse CD8+ T cell epitope sequence (NY p81 or NY p82) and a mouse CD4+ T cell epitope sequence (NY p91) that are derived from human NY-ESO-1 antigen, were synthesized. As the interepitope sequence between epitopes, the native amino acid sequence of NY-ESO-1 was retained in the ESO1 LP (native type) and the sequence of six consecutive tyrosines (Y6) was used in the ESO1 LP (Y6). Vaccines containing the respective long chain peptide antigens were administered to mice in the same manner as in FIG. 1 and the frequencies of CD8+ T cells and CD4+ T cells specific to the respective epitope sequences were measured by the intracellular cytokine staining method.

In many cases with a long chain peptide vaccine, a native amino acid sequence of the protein that is the target antigen is used as it is as the sequence of the long chain peptide antigen. On the other hand, test results up to now have revealed that, depending on the sequence between epitopes, the preceding and subsequent epitopes do not function appropriately (FIGS. 1 to 3). It was thus considered that even if the interepitope sequence is a native amino acid sequence, it may have an unfavorable influence on the functions of the preceding and subsequent epitopes. Thus, the long chain peptide antigen ESO1 LP (native type) and a long chain peptide antigen ESO1 LP ($Y_6$), both containing a mouse CD8+ T cell epitope sequence (NY p81 or NY p82) and a mouse CD4+ T cell epitope sequence (NY p91) that are derived from human NY-ESO-1 antigen, were synthesized. As the sequence between epitopes, the native amino acid sequence of NY-ESO-1 was retained with ESO1 LP (native type) and the sequence of six consecutive tyrosines ($Y_6$) was used with ESO1 LP ($Y_6$). When vaccines containing the respective long chain peptide antigens were administered to mice, whereas the induction of NY p81 specific CD8+ T cells was hardly observed with the vaccine having ESO1 LP (native type) as the antigen, the induction was significant with the vaccine having ESO1 LP ($Y_6$) as the antigen (FIG. 5). Although ESO1 LP (native type) and ESO1 LP ($Y_6$) differ in containing NY p81 (RGPESRLL (Sequence No. 29)) and NY p82 (GPESRLL (Sequence No. 35)), respectively, as the CD8+ T cell epitope, it has been confirmed that NY p82 is poorer in immunogenicity than NY p81 (Non-Patent Document 8) and the excellence of ESO1 LP ($Y_6$) over ESO1 LP (native type) is not due to this difference. Also, the induction of NY p91 specific CD4+ T cells was clearly observed with both ESO1 LP (native type) and ESO1 LP ($Y_6$). From the above, it has been revealed that there are cases where an interepitope sequence derived from a native amino acid sequence does not function and that this problem can be resolved by selecting a consecutive tyrosine sequence as the interepitope sequence.

Figure 6:
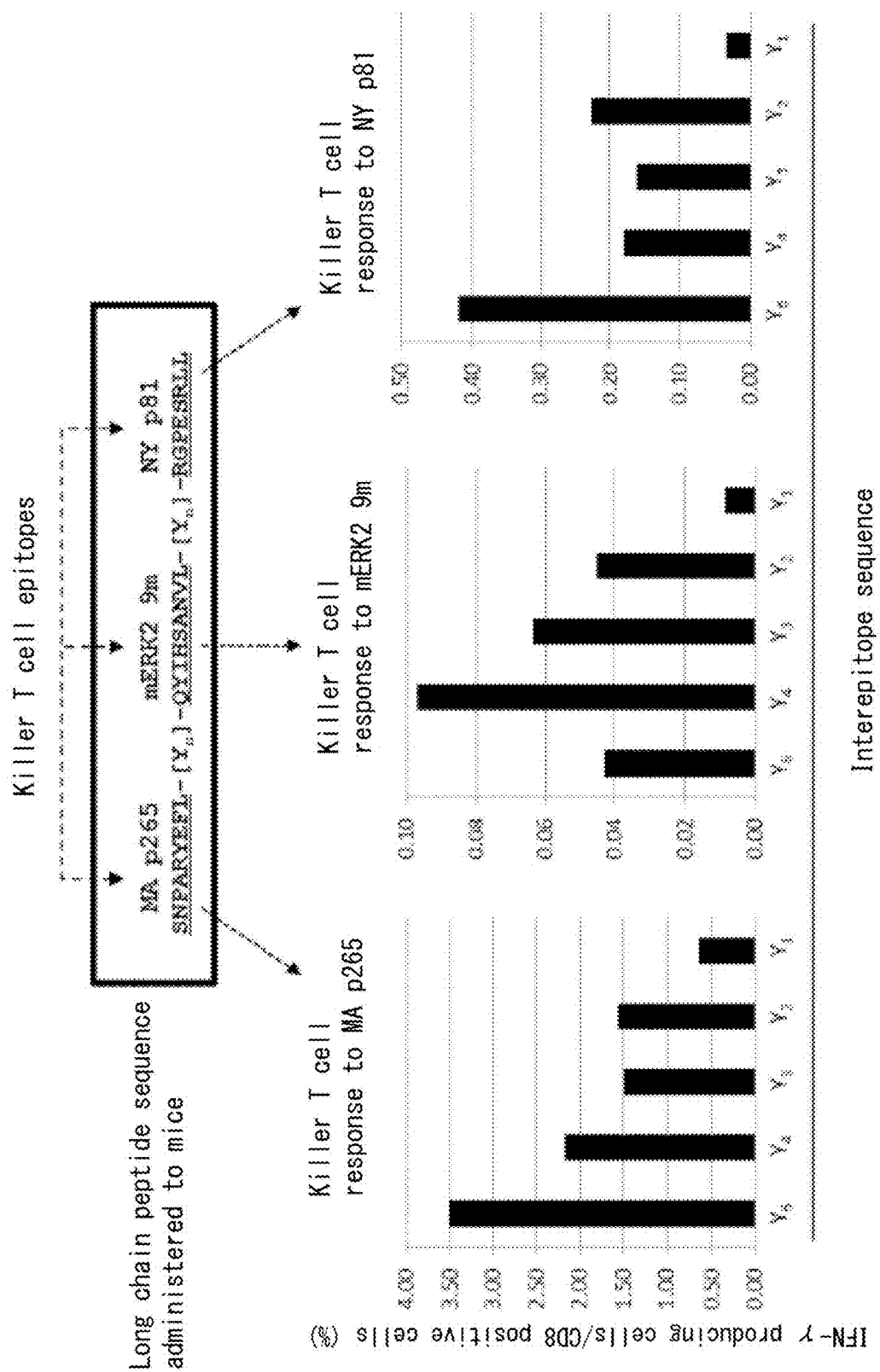
FIG. 6 shows, for interepitope sequences constituted of consecutive tyrosines, the relationship between the number of tyrosines and specific T cell induction by vaccines was examined. Long chain peptide antigens MEN, all containing three types of mouse CD8+ T cell epitope sequences (MA p265 (Sequence No. 27), NY p81 (Sequence No. 29), and mERK2 9m (Sequence No. 28)), were synthesized. The interepitope sequences between the respective epitopes were one to six consecutive tyrosines (Sequence Nos. 1 and 9-12). Vaccines containing the respective long chain peptide antigens were administered to mice in the same manner as in FIG. 1 and the frequencies of CD8+ T cells specific to the respective epitope sequences were measured by the intracellular cytokine staining method.
Figure 7:
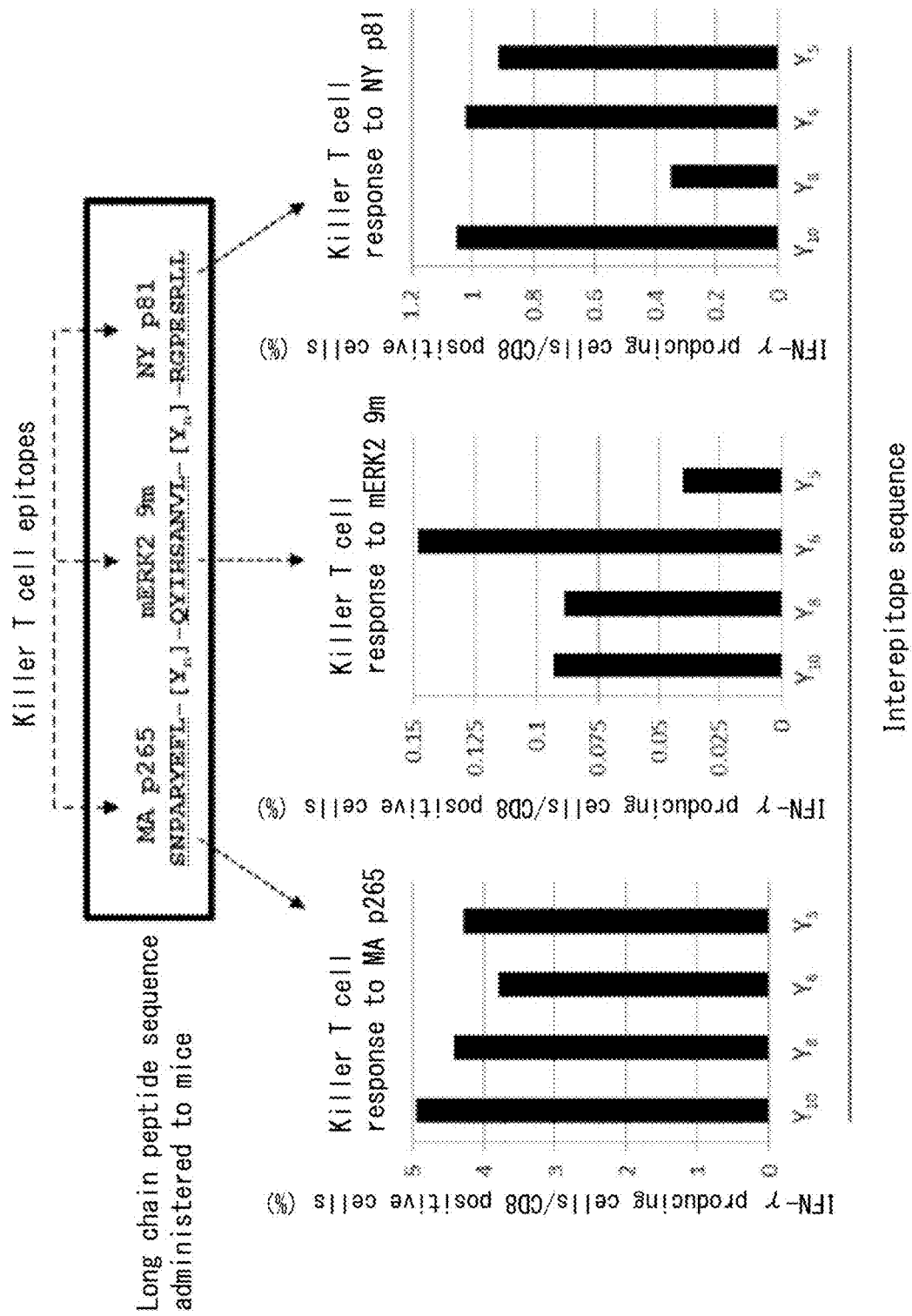
FIG. 7 shows, for interepitope sequences constituted of consecutive tyrosines, the relationship between the number of tyrosines and specific T cell induction by vaccines were examined. Long chain peptide antigens MEN, all containing three types of mouse CD8+ T cell epitope sequences (MA p265 (Sequence No. 27), NY p81 (Sequence No. 29), and mERK2 9m (Sequence No. 28)), were synthesized. The interepitope sequences between the respective epitopes were five to ten consecutive tyrosines (Sequence Nos. 1 and 13-15). Vaccines containing the respective long chain peptide antigens were administered to mice in the same manner as in FIG. 1 and the frequencies of CD8+ T cells specific to the respective epitope sequences were measured by the intracellular cytokine staining method.

Deeming that a sequence of consecutive tyrosines is useful as an interepitope sequence, the optimal number thereof was examined. The long chain peptide antigens MEN, all containing three types of mouse CD8+ T cell epitope sequences (MA p265, NY p81, and mERK2 9m), were synthesized. The sequence between the respective epitopes was set to one to six (FIG. 6) or five to ten (FIG. 7) consecutive tyrosines. Vaccines containing the respective long chain peptide antigens were administered to mice in the same manner as in FIG. 1 and the frequencies of the induced CD8+ T cells were measured. In the case of comparing one to six tyrosines (FIG. 6), in regard to MA p265, which is the first epitope, and NY p81, which is the third epitope, the induction of specific CD8+ T cells was highest when the interepitope sequence was six tyrosines ($Y_6$) and there was a tendency for CD8+ T cell induction to weaken with decrease in the number of tyrosines. In regard to mERK2 9m, which is the second epitope, the induction of specific CD8+ T cells was highest when the interepitope sequence was four tyrosines ($Y_4$) and there was a tendency for CD8+ T cell induction to weaken with decrease in the number of tyrosines. With this mERK2 9m, when the interepitope sequence was six tyrosines ($Y_6$), although lower than that in the case of four tyrosines ($Y_4$), induction of specific CD8+ T cells was observed to some degree. In view of the above results for the three types of epitopes, it was considered that six is best as the number of tyrosines of the interepitope sequence, four comes next and is satisfactory, and three or less is not favorable. In the case of comparing five to ten tyrosines (FIG. 7), in regard to MA p265, which is the first epitope, a clear influence of the number of tyrosines of the interepitope sequence on the induction of specific CD8+ T cells was not observed. In regard to mERK2 9m, which is the second epitope, the induction of specific CD8+ T cells was highest when the interepitope sequence was six tyrosines ($Y_6$) and there was a tendency for CD8+ T cell induction to weaken when the number of tyrosines was other than six. In regard to NY p81, which is the third epitope, a clear influence of the number of tyrosines on the induction of specific CD8+ T cells was not observed with the exception of the case where the number of tyrosines of the interepitope sequence was eight ($Y_8$). In view of the results for the three types of epitopes, it was considered that six is best as the number of tyrosines of the interepitope sequence and results do no change much even if the number increases further. From the above, it was revealed that as the number of consecutive tyrosines as the interepitope sequence, four to eight is preferable, four to six is more preferable, and six is especially preferable.

Figure 8:
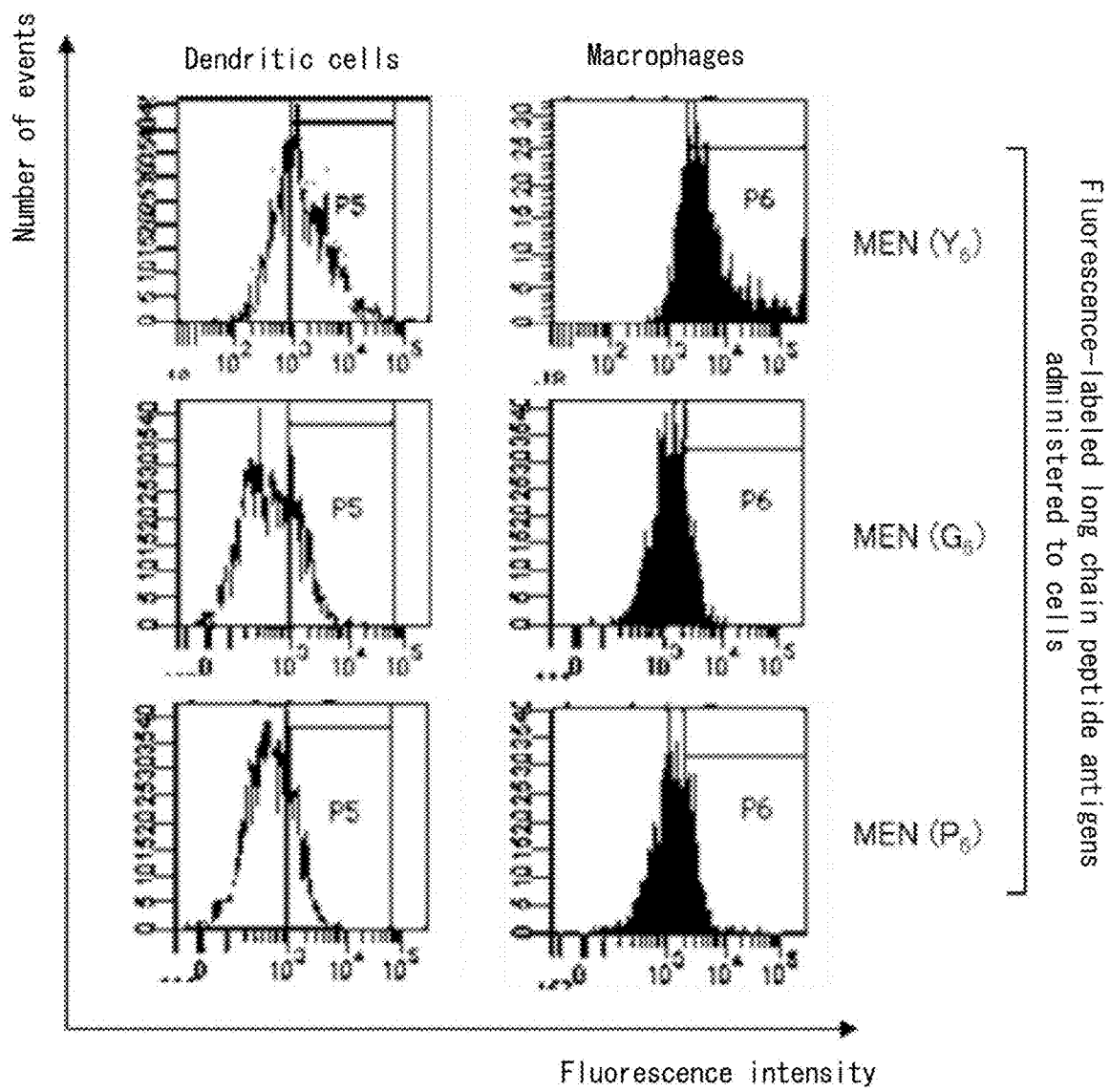
FIG. 8 shows the influences of differences in the interepitope sequences of long chain peptide vaccines on the uptake of the vaccines into antigen-presenting cells were examined. Long chain peptide antigens MEN, all containing three types of mouse CD8+ T cell epitope sequences (MA p265 (Sequence No. 27), NY p81 (Sequence No. 29), and mERK2 9m (Sequence No. 28)), were synthesized. The interepitope sequences between the respective epitopes were respectively six consecutive tyrosines (Y6), six consecutive glycines (G6), or six consecutive prolines (P6) (Sequence Nos. 1-3). Each long chain peptide antigen, labeled with the fluorescent dye FAM, was complexed with CHP and administered in vitro to mouse dendritic cells and mouse macrophages. After 60 minutes, the fluorescence uptakes into the respective cells were measured by flow cytometry with the P5 fraction in the figure being deemed to correspond to the dendritic cells and the P6 fraction in the figure being deemed to correspond to the macrophages.
Figure 9:
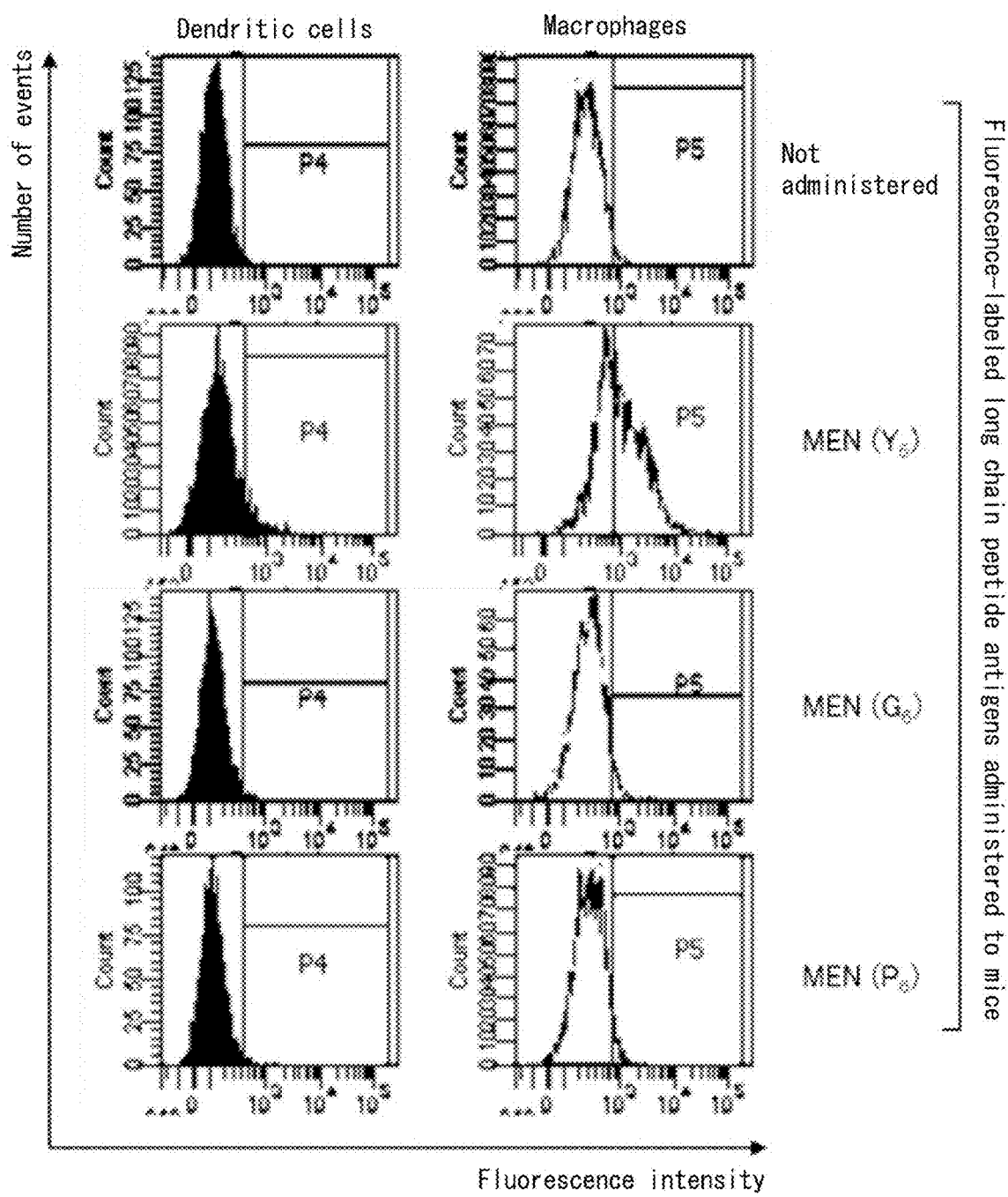
FIG. 9 shows the influences of differences in the interepitope sequences of long chain peptide vaccines on uptake of the vaccines into antigen-presenting cells were examined. The same FAM-labeled long chain peptide antigens as those in FIG. 8 were complexed with CHP and administered subcutaneously to mice. After 16 hours, cells were collected from a regional lymph node of the administration site, and the fluorescence uptakes into dendritic cells and mouse macrophages were measured by flow cytometry with the P4 fraction in the figure being deemed to correspond to the dendritic cells and the P5 fraction in the figure being deemed to correspond to the macrophages.

Deeming that a difference in interepitope sequence influences specific T cell induction by the preceding and subsequent epitopes, a mechanism therefor is believed to be based on whether or not the interepitope sequence is appropriately cleaved by proteasomes, etc., within an antigen-presenting cell (Non-Patent Document 7). In order to explore other mechanisms, long chain peptide antigens MEN, with the interepitope sequence being set to one of six consecutive tyrosines ($Y_6$), glycines ($G_6$), or pralines ($P_6$), were synthesized. Each long chain peptide antigen, labeled with the fluorescent dye FAM, was complexed with CHP and administered in vitro to mouse spleen cells including mouse dendritic cells and macrophages. Upon measuring the fluorescence uptakes into the dendritic cells and macrophage, the unexpected finding that the uptake into cells differs according to differences in the interepitope sequence was obtained (FIG. 8). That is, the long chain peptide antigen adopting $Y_6$ as the interepitope sequence was significantly higher in uptake into cells for both dendritic cells and macrophages in comparison to cases of $G_6$ and $P_6$. A similar finding was also obtained in the test using individual mice. The same FAM-labeled long chain peptide antigens as those in FIG. 8 were complexed with CHP and administered subcutaneously to mice. The fluorescence uptakes into the dendritic cells and mouse macrophages present in the regional lymph node of the administration site were measured. With the macrophages, the uptake of the long chain peptide antigen adopting the $Y_6$ interepitope sequence was clearly observed. In contrast, the uptakes of long chain peptide antigens adopting $G_6$ and $P_6$ were hardly observed. With the dendritic cells, uptake was not observed for any of the long chain peptide antigens. Together with the results in FIG. 8, it was revealed that a long chain peptide antigen with a sequence of consecutive tyrosines as the interepitope sequence is improved in uptake into antigen-presenting cells, especially macrophages. This phenomenon is likely to be mechanism for the highly specific T cell induction ability and excellent cancer treatment effect of a vaccine using a long chain peptide antigen with a sequence of consecutive tyrosines as the interepitope sequence.

Figure 10:
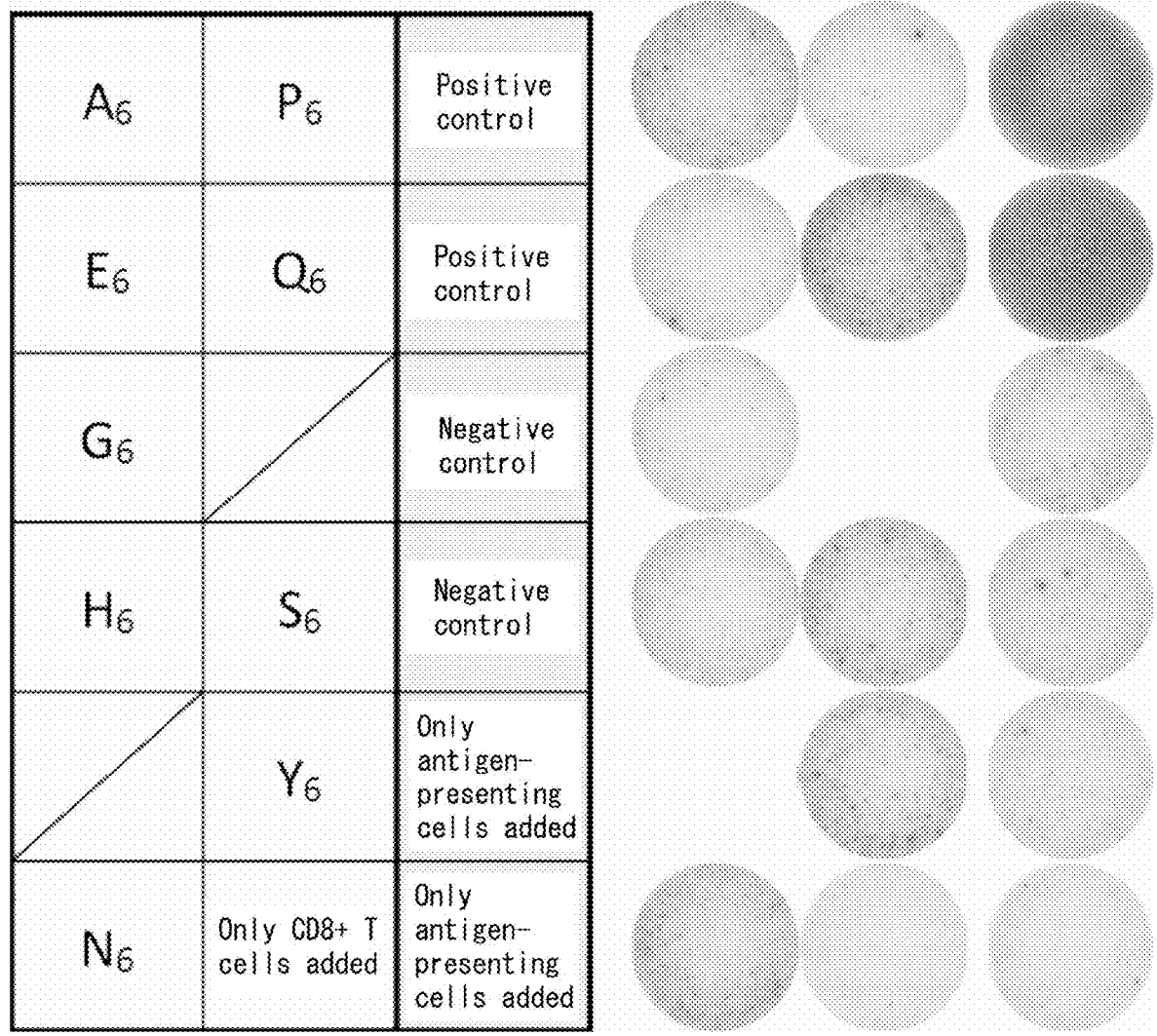
FIG. 10 shows the influences of differences in the interepitope sequences of long chain peptide vaccines, containing a plurality of CD8+ T cell epitopes, on specific CD8+ T cell induction by the vaccines were examined. Long chain peptide antigens NMW, all containing three types of human CD8+ T cell epitope sequences (NY p157:HLA-A0201 restrictive, MA4 p143:HLA-A2402 restrictive, and WT1: HLA-A2402 restrictive p235), were synthesized. The interepitode sequences between the respective epitopes were the six consecutive amino acids shown in FIG. 10, namely Sequence Nos. 18-26. Each long chain peptide antigen was complexed with cholesterol-modified pullulan (CHP), which is a type of delivery system, and administered in vitro as a vaccine to an immortalized human B cell line (LCL). Using these human B cells as the antigen-presenting cells, they were co-cultured with CD8+ T cell clone 1G4 cells specific to NY p157 and the activation of the 1G4 cells due to antigen presentation was measured by an IFN-γ ELISPOT method. As a positive control, LCL administered with an NY p157 short chain peptide was used as the antigen-presenting cells, and as a negative control, LCL without antigen added was used as the antigen-presenting cells.

That with vaccines having a long chain peptide, containing a plurality of T cell epitopes, as an antigen, differences in interepitope sequence influence the success or failure of specific T cell induction by the respective epitopes was examined in in vitro antigen presentation reactions using human immunocytes (FIG. 10). Long chain peptide antigens NMW, all containing the three types of human CD8+ T cell recognition epitope sequences, NY p157, MA4 p143, and WT1 p235, derived from the human tumor antigens, NY-ESO-1, MAGE-A4, and WT1, were synthesized. The sequence between the three types of epitopes was set to that in which six of one of alanine (A), glutamic acid (E), glycine (G), histidine (H), asparagine (N), proline (P), glutamine (Q), serine (S), or tyrosine (Y) are made consecutive. A long chain peptide containing an interepitope sequence constituted of an amino acid besides the above was difficult to synthesize or difficult to complex with CHP. Immortalized human B cell lines (LCL) administered with vaccines prepared by complexing the respective long chain peptide antigens with CHP were used as antigen-presenting cells to evaluate the antigen presenting activity with respect to NY p157 specific CD8+ T cell clone 1G4 cells by the IFN-γ ELISPOT method. As with the examination results with mice, whereas the activation of 1G4 cells was clearly confirmed with the long chain peptide vaccine adopting the $Y_6$ interepitope sequence, the activation of 1G4 cells was not clearly confirmed with the vaccine adopting the $G_6$ or the $P_6$ interepitope sequence. Also, as with the vaccine using $Y_6$, the activation of 1G4 cells was clearly observed with vaccines using $A_6$, $N_6$, $Q_6$, and $S_6$ as the interepitope sequences and it was thus revealed that these interepitope sequences are also useful.

Figure 11:
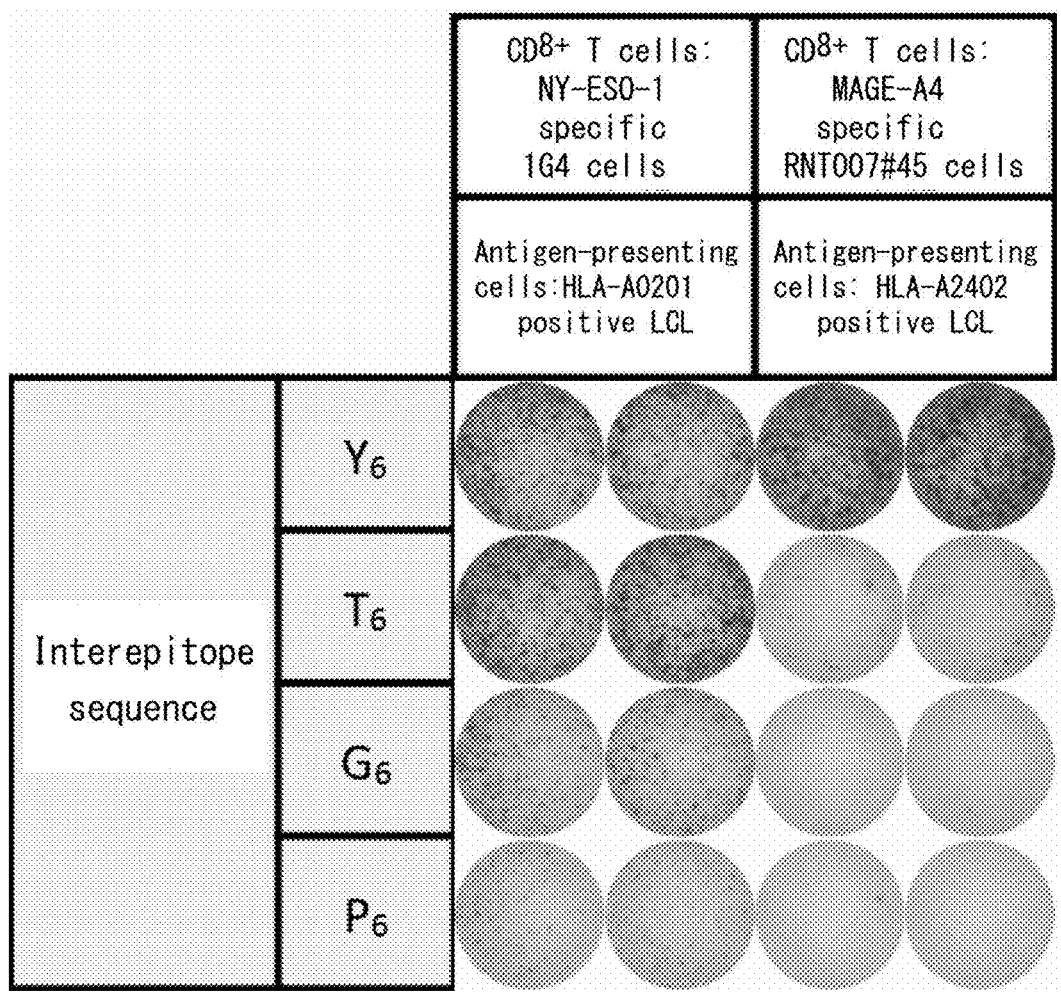
FIG. 11 shows the influences of the differences in the interepitope sequences of RNA vaccines, containing a plurality of CD8+ T cell epitopes, on specific CD8+ T cell induction by the vaccines were examined. mRNAs encoding long chain peptide antigens NMW, all containing three types of human CD8+ T cell epitope sequences (NY p157:HLA-A0201 restrictive, MA4 p143:HLA-A2402 restrictive, and WT1: HLA-A2402 restrictive p235), were synthesized. The interepitode sequences between the respective epitopes were the six consecutive amino acids shown in FIG. 11, namely sequence Nos. 31-34. Each mRNA was introduced in vitro as a vaccine into LCL by electroporation. Using these LCL as the antigen-presenting cells, they were co-cultured with CD8+ T cell clone 1G4 cells specific to NY p157 or CD8+ T cell clone RNT007#45 cells specific to MA4 p143 and the activation of the CD8+ T cells due to antigen presentation was measured by the IFN-γ ELISPOT method.

That with vaccines using mRNA encoding a long chain peptide antigen that contains a plurality of T cell epitopes, differences in interepitope sequence influence the success or failure of specific T cell induction by the respective epitopes was examined in in vitro antigen presentation reactions using human immunocytes (FIG. 11). mRNAs that code long chain peptide antigens NMW, all containing the three types of human CD8+ T cell recognition epitope sequences, NY p157, MA4 p143, and WT1 p235, derived from the human tumor antigens, NY-ESO-1, MAGE-A4, and WT1, were synthesized. The sequence between the three types of epitopes was set to that in which six of one of glycine (G), proline (P), threonine (T), or tyrosine (Y) are made consecutive. LCL with the respective mRNAs introduced therein were used as antigen-presenting cells to evaluate the antigen presenting activity with respect to NY p157 specific CD8+ T cell clone 1G4 cells or MA4 p143 specific CD8+ T cell clone RNT007 #45 cells by the IFN-γ ELISPOT method. Activations of 1G4 cells and RNT007 #45 were clearly confirmed with the RNA vaccine encoding the long chain peptide adopting $Y_6$ as the interepitope sequence. From this, it has been revealed that the interepitope sequence of the present invention is useful not only in peptide vaccines but also in RNA vaccines.

The usefulness of consecutive tyrosines or threonines as an interepitope sequence is not limited to the long chain peptide vaccines described above and may also be applied to DNA vaccines, mRNA vaccines, or dendritic cell vaccines.

A DNA vaccine may be prepared by using artificial gene synthesis techniques to synthesize a cDNA, encoding a long chain peptide antigen having a single methionine at the N-terminus and having a plurality of T cell epitopes linked by consecutive tyrosine sequences or consecutive threonine sequences, and inserting it into a gene expression plasmid vector for mammals. The cDNA of the long chain peptide antigen is synthesized to be in the range of 66 to several kbp according to the number of T cell epitopes to be included. As the plasmid, that which contains pcDNA3, pVAX, or other promoter (CMV promoter, etc.) that operates in mammalian cells, polyA (derived from bovine growth hormone, etc.) for mRNA stabilization, and a drug resistance gene (such as that for kanamycin) may be used. The plasmid may carry a plurality of long chain peptide antigen cDNAs and the respective antigen cDNAs can be co-expressed by linking with an IRES sequence, etc. Similarly, the plasmid may carry, at the same time, accessory genes for enhancing tumor immune response, for example, cytokines such as IFN-γ and IL-12, immunostimulatory molecules, such as GITR ligand-Fc, immunosuppression inhibitors, such as PD-L1-Fc. Also, a plurality of plasmid DNAs that differ in the numbers and types of antigen cDNAs and accessories molecules carried may be administered at the same time.

The DNA vaccine that is obtained is repeatedly administered subcutaneously, intradermally, intravenously, intramuscularly, intralymphnodally, epicutaneously, or intratumorally to the living body of an animal, such as a mouse (BALB/c mouse or C57BL/6 mouse, etc.), or a human, etc., at a dose of 1 µg to 1 mg per individual and an interval of one to four weeks using an administration technique such as a gene gun, needle-free injector, electroporation method, DNA tattooing, delivery system (cationic liposome, polyethylene imine, etc.), hydrodynamic method, transdermal administration method. One to two weeks after administration, the specific T cells induced by the T cell epitopes contained in the long chain peptide antigens that are transcribed and translated from the cDNA on the DNA vaccine may be detected by an immunological technique such as an intracellular cytokine staining method, ELISPOT method, MHC tetramer staining method. In tests using mice, CMS5a fibrosarcoma, CT26 colorectal cancer, 4T1 breast cancer (hereabove in the case of BALB/c mouse), B16 melanoma, or LLC lung cancer (hereabove in the case of C57BL/6 mouse) incorporating a wild type or model antigen gene may be implanted subcutaneously to observe the inhibitory effect of the DNA vaccine against growth and metastasis of the tumor. Tumor growth may be measured by measuring the size of the tumor or, if tumor cells incorporating a monitor gene such as a luciferase gene, are used, by an in vivo imaging technique, such as IVIS (PerkinElmer Inc.), etc. To evaluate metastasis, tumor nodules, which, upon intravenous or subcutaneous administration of tumor, occur in the lungs, etc., that are the metastasis destinations, may be visually counted after dissection or be evaluated by an in vivo imaging technique.

With a DNA vaccine, a biological vector using a virus or microorganism may be used instead of a plasmid vector. As a viral vector, a retroviral vector, lentiviral vector, adenoviral vector, adeno-associated virus vector, vaccinia virus vector, fowlpox virus vector, alphavirus vector, or Sendai virus vector, etc., may be used. As a microorganism vector, yeast, *Listeria*, *Salmonella*, *E. coli*, or *Lactobacillus*, etc., may be used. A DNA vaccine using such a biological vector is administered intravenously, subcutaneously, intradermally, intramuscularly, intralymphnodally, supramucosally, or intratumorally to a test animal, such as a mouse, or a human. The arrangement and evaluation methods (immunogenicity and therapeutic effects) of the genes carried on the biological vector are the same as in the example of the plasmid vector described above.

An mRNA vaccine encoding consecutive tyrosines or threonines as the interepitope sequence may be implemented in the same manner as a DNA vaccine. Artificial gene synthesis techniques are used to synthesize a cDNA, encoding a long chain peptide antigen having a single methionine at the N-terminus and having a plurality of T cell epitopes linked by consecutive tyrosine sequences or consecutive threonine sequences, and inserting it into a template plasmid DNA for in vitro transfer. The cDNA is prepared to be in the range of 66 to several kbp according to the number of T cell epitopes to be included. As the plasmid DNA, that which contains a promoter (T7 promoter, T3 promoter, SP6 promoter, etc.) recognized by a phage RNA polymerase, polyA, and a drug resistance gene (such as that for kanamycin), that is for example, pGEM or pcDNA3, etc., may be used. Using this plasmid DNA as a template, an mRNA is synthesized using a commercially available in vitro transfer kit (MEGAscript, made by Life Technologies, Inc., or RiboMax Large Scale RNA Production Systems, made by Promega Corporation, etc.). polyA is added to the mRNA as necessary using a polyA tailing kit (Life Technologies, Inc.), etc. The mRNA obtained is administered subcutaneously, intradermally, intramuscularly, intralymphnodally, or intratumorally as it is or upon stabilizing with a protamine or liposome, etc., to a test animal, such as a mouse, or a human. The mRNA vaccine may contain a plurality of mRNAs. For example, a plurality of mRNAs that code long chain peptide antigens may be administered upon mixing. An mRNA encoding accessory molecules for enhancing tumor immune response, for example, cytokines such as IFN-γ and IL-12, immunostimulatory molecules, such as CD40 ligand and GITR ligand-Fc, immunosuppression inhibitors, such as PD-L1-Fc, may be administered at the same time as the mRNA vaccine. The administration conditions and evaluation methods (immunogenicity and therapeutic effects) of the mRNA vaccine are the same as in the example of the DNA vaccine described above.

Dendritic cells to be used in a dendritic cell vaccine may be induced to differentiate in vitro from peripheral blood mononuclear cells in the case of humans and bone marrow cells in the case of mice by a conventional method using GM-CSF and IL-4. A long chain peptide antigen described above or an mRNA encoding a long chain peptide antigen described above is added to the cells to prepare a vaccine. If a long chain peptide antigen is used, the efficiency of uptake and expression can be increased by using CHP as a delivery system (FIG. 8). If an mRNA encoding a long chain peptide antigen is used, the efficiency of uptake and expression in dendritic cells can be increased by electroporation method. In this process, an mRNA encoding an accessory molecule for enhancing tumor immune response may be added at the same time as described above. The dendritic cells after addition of antigen may be used upon being stimulated and matured by TNFα, IL-1β, IL-6, Flt3 ligand, $PGE_2$, CpG oligo DNA, poly IC RNA, etc. The dendritic cell vaccine obtained is administered subcutaneously, intradermally, intralymphnodally, intratumorally, or intravenously to a test animal, such as a mouse, or a human at a dose of $10^6$ to $10^8$ cells. The evaluation methods (immunogenicity and therapeutic effects) are the same as in the example of the DNA vaccine described above.

A long chain peptide vaccine, DNA vaccine, mRNA vaccine, or dendritic cell vaccine adopting consecutive tyrosines or threonines as the interepitope sequence may be applied to diseases other than cancer, for example, to infectious diseases. As pathogens of infections, pathogenic viruses, such as hepatitis virus, human papilloma virus, adult T-cell leukemia virus, human immunodeficiency virus, herpes virus, influenza virus, Coxsackie virus, rotavirus, RS virus, varicella zoster virus, measles virus, polio virus, norovirus, pathogenic obligate intracellular parasitic microorganisms, such as rickettsia, chlamydia, phytoplasma, Coxiella, Toxoplasma, Leishmania, protozoa, such as Plasmodium, Cryptosporidium, can be cited.

For example, for a vaccine against the hepatitis C virus, a long chain peptide antigen may be designed with which a plurality of T cell epitopes, identified in hepatitis C virus-derived proteins, such as the core protein, NS4, and NS3, are linked with an interepitope sequence constituted of consecutive tyrosines or threonines. Administration conditions of the vaccine containing the long chain peptide antigen and therapeutic effects on hepatitis C virus infection may be examined using a model system, such as an immunodeficient mouse transplanted with human liver tissue. Similarly, for a vaccine against human herpesvirus, a long chain peptide antigen may be designed using T cell epitopes contained in the human herpesvirus-derived proteins E6 and E7, and administration conditions and therapeutic effects may be examined with a mouse model transplanted with a tumor that expresses E6 or E7. For a vaccine against a pathogenic microorganism, for example, for a vaccine against malaria, a long chain peptide antigen is designed with which a group of T cell epitopes, contained in merozoite surface protein 3 (MSP3) and glutamate rich protein (GLURP), which are expressed on the surface of the mature body of Plasmodium, and liver-specific protein 2 (LISP2), which is expressed in the intracanal air, are linked with a sequence of consecutive tyrosines or a sequence of consecutive threonines. A mouse administered with a vaccine containing the long chain peptide antigen, is intravenously administered with 10,000 Plasmodium sporozoites and a peripheral blood smear is prepared 4 to 14 days later. Administration conditions and therapeutic effects of the vaccine may be examined by staining with Giemsa and thereafter observing the parasitemia under a microscope.

The above results show on one hand that differences in interepitope sequence have a large influence on specific T cell induction by a plurality of epitopes contained in a long chain peptide antigen and that a cancer treatment vaccine using an inappropriate interepitope sequences is poor in inducing the intended T cells and in cancer treatment effect, and show on the other hand that by using consecutive tyrosines or threonines as the interepitope sequence, specific T cell induction by the plurality of epitopes contained in the long chain peptide antigen can be achieved reliably and a cancer treatment vaccine that exhibits high treatment effects can be realized. In the process, it has been revealed that the effects are exhibited regardless of the epitope sequences preceding and subsequent the interepitope sequence and it was also possible to define the optimal length of the interepitope sequence.

According to the present embodiments, it was possible to provide cancer treatment vaccines of extremely high cancer treatment effects.

The invention claimed is:

1. A peptide comprising:
   a first killer or helper T-cell recognition epitope,
   a second killer or helper T-cell recognition epitope and
   a first interepitope sequence that is located between the first and second killer or helper T-cell recognition epitopes, the first interepitope sequence consisting of four to ten consecutive tyrosines,
   wherein the killer T-cell recognition epitopes form complexes with MHC class I molecules and are recognized by CD8+ killer T-cells when said complexes are presented on the surfaces of antigen-presenting cells,
   wherein the helper T-cell recognition epitopes form complexes with MHC class II molecules and are recognized by CD4+ helper T-cells when said complexes are presented on the surfaces of antigen-presenting cells, and
   wherein the first interepitope sequence mediates enhanced uptake of the peptide into antigen-presenting cells.

2. The peptide as claimed in claim 1, wherein the peptide also has:
   a third killer or helper T-cell recognition epitope and a second interepitope sequence that is located between the second and third killer or helper T-cell recognition epitopes, the second interepitope sequence consisting of four to ten consecutive tyrosines.

3. A pharmaceutical composition comprising the peptide as claimed in claim 1 and a hydrophobized polysaccharide.

4. The pharmaceutical composition as claimed in claim 3, wherein the hydrophobized polysaccharide is cholesterol-modified pullulan (CHP).

5. The pharmaceutical composition as claimed in claim 4, wherein the first and second killer or helper T-cell recognition epitopes are derived from at least one shared cancer antigenic protein and the peptide elicits an anti-tumor response in an animal or a human.

6. The peptide as claimed in claim 1, wherein the antigen-presenting cells are dendritic cells and macrophages.

7. The pharmaceutical composition as claimed in claim 4, wherein the first and second killer or helper T-cell recognition epitopes are derived from at least one neoantigen generated by a gene mutation.

8. The pharmaceutical composition as claimed in claim 6, further comprising an adjuvant.

9. The pharmaceutical composition as claimed in claim 8, wherein the adjuvant is CpG oligo DNA.

10. A pharmaceutical composition, wherein the pharmaceutical composition comprises the peptide of claim 1, the first and second recognition epitopes respectively comprise different amino acid sequences found in one or more tumor-associated antigens, and the peptide elicits an anti-tumor response in an animal or a human.

11. The pharmaceutical composition as claimed in claim 10, wherein the first and second killer T-cell recognition epitopes consist of 8-10 amino acids and the first and second helper T-cell recognition epitopes consist of 15-20 amino acids.

12. The peptide as claimed in claim 1, wherein the first and second recognition epitopes are adjacent to the interepitope sequence.

13. The peptide as claimed in claim 12, wherein the antigen-presenting cells are dendritic cells and macrophages.

14. A pharmaceutical composition comprising the peptide as claimed in claim 12 and a hydrophobized polysaccharide.

15. The pharmaceutical composition as claimed in claim 14, wherein the hydrophobized polysaccharide is cholesterol-modified pullulan (CHP).

16. The pharmaceutical composition as claimed in claim 15, further comprising an adjuvant.

17. The pharmaceutical composition as claimed in claim 16, wherein the adjuvant is CpG oligo DNA.

18. A pharmaceutical composition, wherein the pharmaceutical composition comprises the peptide of claim 1, the first and second recognition epitopes respectively comprise different amino acid sequences found in one or more antigens of an infection-causing pathogen, and the peptide elicits an immune response against the infection-causing pathogen in an animal or a human.

19. The peptide as claimed in claim 12, wherein the first interepitope sequence consists of six to ten consecutive tyrosines.

20. A pharmaceutical composition, wherein the pharmaceutical composition comprises the peptide of claim 12, the first and second recognition epitopes respectively comprise different amino acid sequences found in one or more tumor-associated antigens, and the peptide elicits an anti-tumor response in humans.

21. A pharmaceutical composition, wherein the pharmaceutical composition comprises the peptide of claim 12, the first and second recognition epitopes respectively comprise different amino acid sequences found in one or more antigens of an infection-causing pathogen, and the peptide elicits an immune response against the infection-causing pathogen in an animal or human.

22. The peptide as claimed in claim 1, wherein the peptide is a synthetic peptide and not a full-length recombinant protein.

23. The peptide as claimed in claim 12, wherein the peptide is a synthetic peptide and not a full-length recombinant protein.

\* \* \* \* \*